United States Patent
Bridgeman

(10) Patent No.: US 12,116,564 B2
(45) Date of Patent: *Oct. 15, 2024

(54) CELLS EXPRESSING RECOMBINANT GROWTH FACTOR RECEPTORS

(71) Applicant: INSTIL BIO (UK) LIMITED, Manchester (GB)

(72) Inventor: John Stephen Bridgeman, Manchester (GB)

(73) Assignee: INSTIL BIO (UK) LIMITED, Manchester (GB)

( * ) Notice: Subject to any disclaimer, the term of this patent is extended or adjusted under 35 U.S.C. 154(b) by 0 days.

This patent is subject to a terminal disclaimer.

(21) Appl. No.: 18/068,319

(22) Filed: Dec. 19, 2022

(65) Prior Publication Data

US 2023/0212511 A1 Jul. 6, 2023

Related U.S. Application Data

(63) Continuation of application No. 16/061,435, filed as application No. PCT/GB2016/053949 on Dec. 15, 2016, now Pat. No. 11,530,386.

(30) Foreign Application Priority Data

Dec. 15, 2015 (GB) .................................... 1522097

(51) Int. Cl.
| | | |
|---|---|---|
| *C07K 14/705* | (2006.01) | |
| *A61K 31/415* | (2006.01) | |
| *A61K 39/00* | (2006.01) | |
| *C07K 14/71* | (2006.01) | |
| *C07K 14/715* | (2006.01) | |
| *C07K 14/72* | (2006.01) | |
| *C12N 5/00* | (2006.01) | |
| *C12N 5/0783* | (2010.01) | |
| *C12N 15/86* | (2006.01) | |

(52) U.S. Cl.
CPC .......... *C12N 5/0636* (2013.01); *A61K 31/415* (2013.01); *A61K 39/4611* (2023.05); *A61K 39/4613* (2023.05); *A61K 39/464402* (2023.05); *A61K 39/464403* (2023.05); *C07K 14/70596* (2013.01); *C07K 14/71* (2013.01); *C07K 14/715* (2013.01); *C07K 14/7153* (2013.01); *C07K 14/72* (2013.01); *C12N 15/86* (2013.01); *C07K 2319/03* (2013.01); *C07K 2319/033* (2013.01); *C12N 2510/00* (2013.01); *C12N 2740/15043* (2013.01); *C12N 2740/15052* (2013.01)

(58) Field of Classification Search
CPC ......... C07K 14/705; C07K 14/71; C12N 5/00
See application file for complete search history.

(56) References Cited

U.S. PATENT DOCUMENTS

| | | | | |
|---|---|---|---|---|
| 11,530,386 B2* | 12/2022 | Bridgeman | .......... | C12N 5/0636 |
| 2010/0240033 A1* | 9/2010 | Goffin et al. | ............ | C12Q 1/68 |
| | | | | 435/6 |

* cited by examiner

*Primary Examiner* — Teresa E Knight
*Assistant Examiner* — James Joseph Graber
(74) *Attorney, Agent, or Firm* — Alston & Bird LLP

(57) ABSTRACT

The present invention discloses cell lines and recombinant growth factor receptors useful in adoptive cell therapy (ACT), wherein the recombinant growth factor receptor can act as a molecular switch enabling cells expressing the rGFR protein to be expanded in-vitro or in-vivo. Thus the invention provides a T or NK cell, comprising a recombinant growth factor receptor (rGFR) comprising: (i) an extracellular (EC) domain; (ii) a thrombopoietin receptor transmembrane (TM) domain; and (iii) a growth factor receptor intracellular (IC) domain.

12 Claims, 8 Drawing Sheets

Figure 1:
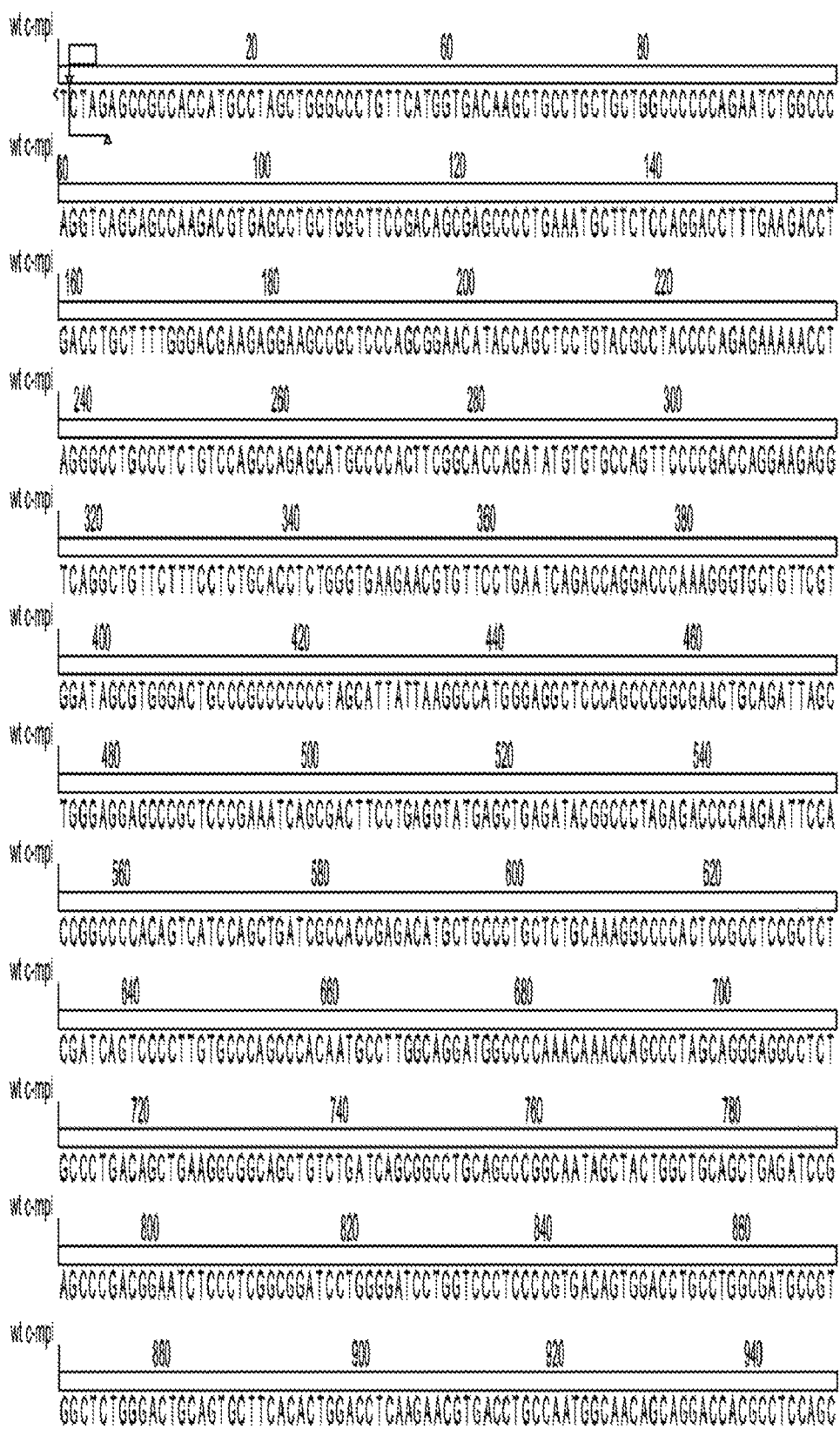

Specification includes a Sequence Listing.

wt c-mpl 940 960 1000 1020
CAGGGCTTCTTCTATGACAGCAGAGCCAGGTGTTGCCCTAGGGACAGATATCCCATCTGGGAGAACTGCGAGGAGGAGG wt c-mpl 1040 1060 1080 1100
AAAAGACCAATCCCGGCCTGCAGACCCCCCAGTTCAGCAGATGCCACTTTAAAAGCAGGAACGACTCCATCATCCACAT wt c-mpl 1120 1140 1160 1180
CCTGGTGGAAGTGACCACAGCCCCCGGCACAGTGCACTCCTACCTGGGCAGCCCCTTTTGGATCCAGCAGGCCGTGAGG wt c-mpl 1200 1220 1240 1260
CTGCCCACAGCCAATCTGCACTGGAGAGAAATCTCCAGCGGCCACCTGGAGCTCGAGTGGCAACACCCCTCCAGCTGGG wt c-mpl 1280 1300 1320 1340
CCGCTCAGGAGACCTGCTACCAGCTGAGGTATACCGGCGAGGGCACCAGGACTGGAAGGTGCTGGAGCCTCCTCTGGG wt c-mpl 1360 1380 1400 1420
AGCTAGAGGCGGCACACTCGAGCTGAGACCTAGGAGCAGGTATAGACTGCAGCTGAGGGCCAGGCTGAACGGACCCACA wt c-mpl 1440 1460 1480 1500
TACCAGGGACCCTGGTCCAGCTGGTCCGATCCCACCAGAGTGGAAACCGCTACCGAGACAGCTTGGATCTCCCTCGTGA wt c-mpl 1520 1540 1560 1580
CCGCTCTGCACCTGGTGCTGGGACTCTCCGCCGTGCTGGGACTGCTGCTGCTGAGGTGGCAATTCCCCGCTCACTACAG wt c-mpl 1600 1620 1640
GAGGCTGAGACACGGTCTGTGGCCCTCCCTCCCCGACCTGCATAGAGTGCTCGGCCAGTACCTCAGGGATACCGCCGCT wt c-mpl 1660 1680 1700 1720
CTGAGGCCTCCTAAGGCCACCGTGAGCGACACATGCGAGGAGGTCGAGCCCTCCTCCTGGAGATCCTGCCCAAAAGCA wt c-mpl 1740 1760 1780 1800
GCGAGAGAACCCCCCTGCCCCTGTGTAGCAGCCAAGCCCAGATGGACTACAGGAGACTGCAGCCTTCCTGCCTCGGAAC wt c-mpl 1820 1840 1860 1880
CATGGCCCTGTCGGTCTGCCCTCCTATGGCTGAGTCCGGCAGCTGTTGCACCAGCCATATCGCTAACCACAGCTACCTC wt c-mpl 1900 1920
CCTCTGTCCTACTGGCAGCAGCCCTGATGAGCTAGC

Fig. 1 (continued)

CELLS EXPRESSING RECOMBINANT GROWTH FACTOR RECEPTORS

CROSS-REFERENCE TO RELATED APPLICATIONS

This application is a continuation of U.S. application Ser. No. 16/061,435 filed Jun. 12, 2018, which is a national stage entry of PCT/GB2016/053949 filed Dec. 15, 2016, which claims priority to GB application no. 1522097.3 filed Dec. 15, 2015, which is hereby incorporated by reference.

REFERENCE TO SEQUENCE LISTING

This application includes an electronic sequence listing in a file named 588508SEQLIST.XML, created on Nov. 22, 2022, and containing 24,835 bytes, which is hereby incorporated by reference in its entirety for all purposes.

FIELD OF THE INVENTION

The present invention relates to a cell comprising a recombinant growth factor receptor (rGFR) useful in adoptive cell therapy (ACT). The recombinant growth factor receptor can act as a molecular switch enabling cells expressing the rGFR protein to be expanded in-vitro or in-vivo. The present invention also provides rGFR proteins, nucleic acid encoding the rGFRs, and therapeutic uses thereof.

BACKGROUND TO THE INVENTION

Adoptive cell therapy (ACT) using autologous T-cells to mediate cancer regression has shown much promise in early clinical trials. Several general approaches have been taken such as the use of naturally occurring tumour reactive or tumour infiltrating lymphocytes (TILs) expanded ex vivo. Additionally, T-cells may be modified genetically to retarget them towards defined tumour antigens. This can be done via the gene transfer of peptide (p)-major histocompatibility complex (MHC) specific T-cell Receptors (TCRs) or synthetic fusions between tumour specific single chain antibody fragment (scFv) and T-cell signalling domains (e.g. CD3), the latter being termed chimeric antigen receptors (CARs). TIL and TCR transfer has proven particularly good when targeting Melanoma (Rosenberg et al. 2011; Morgan 2006), whereas CAR therapy has shown much promise in the treatment of certain B-cell malignancies (Grupp et al. 2013).

The current general treatment protocol for ACT requires an initial non-myeloablative preconditioning treatment using cyclophosphamide and/or fludarabine which removes most of the circulating lymphocytes in the patients prior to reinfusion of the ex vivo grown cells. This allows space for the new cells to expand and removes potential 'cytokine sinks' by which normal cells compete with the newly infused cells for growth and survival signals. Along with the cells patients receive cytokine support via infusions of high doses of interleukin(IL)-2 which helps the new cells engraft and expand.

There are a number of factors which currently limit the technology of T-cell ACT. Current preconditioning therapy described above requires hospital admission and potentially leaves patients in an immunocompromised state. Furthermore, many patients are not in a healthy enough state to be able to withstand the rigours of this treatment regimen. Beyond preconditioning the use of IL-2 as a supportive therapy is associated with severe toxicity and potential intensive care treatment. Indeed, TIL therapy itself, unlike TCR and CAR therapy, has not been associated with any serious on or off target toxicities, with the majority of toxicity events being associated with the accompanying IL-2 infusions.

Methods by which preconditioning and IL-2 supportive treatments can be minimised or reduced will have major benefits in that they will: (i) reduce patient hospitalisation, (ii) increase the proportion of potential patients who could be treated by ACT, (iii) reduce the clinical costs associated with extensive hospital admission, thus again opening up the possibility of ACT to more patients.

Thus there is a need for new ACT therapies that minimise the need for preconditioning treatments and/or IL-2 supportive treatments.

The present invention uses cells that express a recombinant growth factor receptor which can be turned on or off by the administration of a ligand for the rGFR, which may be a clinically validated drug. This permits expansion of target cells in-vivo with minimal toxicity to other cells.

A number of reports have used the idea of growth factor receptor engineering as a means of expanding certain populations of cells or for the development of selection processes for antibody engineering strategies. For example, a number of reports have demonstrated that antibody-TpoR or EpoR fusions could be used to for a number of biotechnology strategies such as single chain antibody selections (Ueda et al. 2000, Kawahara et. Al. 2004), and a number of reports have demonstrated that growth factor receptor fusions can successfully expand the megakaryocyte cell line Ba/F3 and/or haematopoietic stem cells (Jin et al. 2000; Richard et al. 2000; Nagashima et al. 2003; Kawahara et al 2011; Saka et al. 2013).

The thrombopoietin (Tpo) receptor (TpoR; CD110, c-mpl) is normally expressed in cells of the megakaryocyte lineage. In its normal state the TpoR is switched on in response to thrombopoietin, which causes megakaryocyte production of platelets. There is also an active negative feedback loop by which platelet expression of TpoR can be used as a sink to reduce circulating levels of Tpo. Importantly TpoR is not expressed on any other normal tissue or cancer cells (Columbyova 1995).

However, there have been no reports of T-cells, or other lymphocytes, being engineered to express rGFRs, such as TpoR or a mutant thereof, and no reports of the use of these cells in ACT.

FIGURES

FIG. 1—Codon optimised sequence of c-mpl (TpoR). Sequence (SEQ ID NO:11) shows the entire open reading frame of the c-mpl (TpoR).

Figure 2:
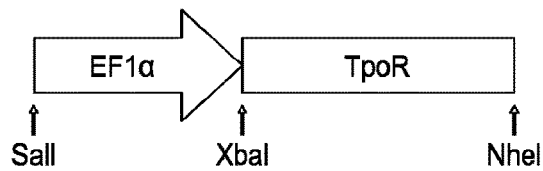

FIG. 2—Schematic representation of the gene organisation of the lentiviral transgene. The TpoR transgene was codon optimised and cloned downstream of the EF1α promoter by way of an Xbal and Nhel restriction digest pair in the pSF.Lenti Lentiviral vector.

Figure 3:
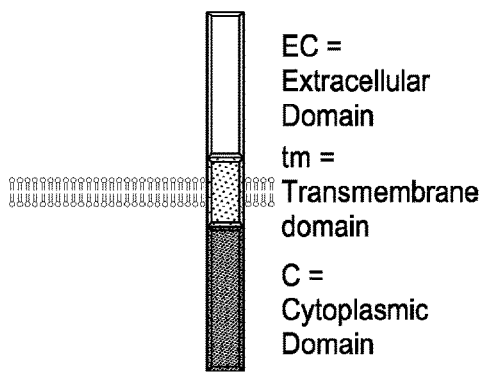

FIG. 3—Schematic representation of modular T-cell growth signal receptor. EC consists of an extracellular domain which may be derived from a native growth factor receptor, a single chain antibody or selectable marker such as CD34. Tm comprises a transmembrane sequence which anchors the polypeptide to the cell surface membrane. The Tm sequence would be derived from the human thrombopoietin receptor. C consists of a cytoplasmic domain derived from a wild type or mutated growth factor receptor.

Figure 4:
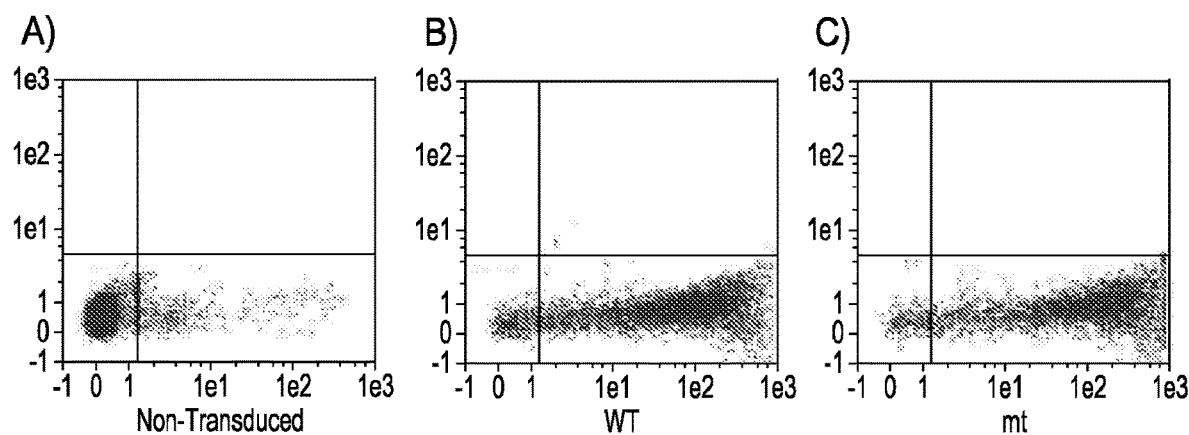

FIG. 4—Flow analysis of non-transduced, wildtype (WT) and mutant truncated (mt) TpoR expression in primary human T-cells. Primary human T-cells were transduced with lentiviral particles carrying the indicated transgenes. Expression was assessed 72 h post infection using anti-CD110-PE antibodies.

Figure 5:
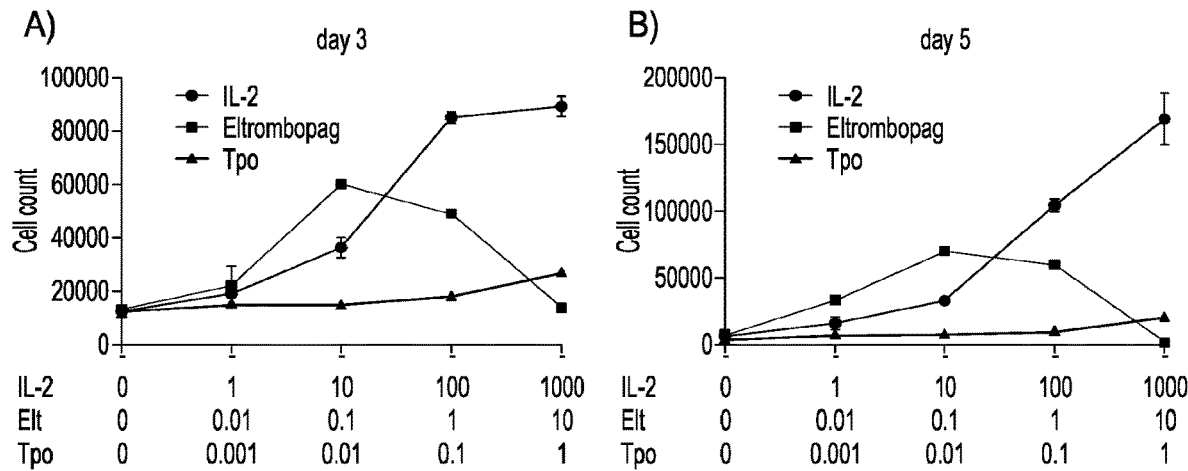

FIG. 5—Analysis of responsiveness of modular T-cell growth signal receptor engineered T-cells to varying concentrations of IL-2, Eltrombopag (Elt) or thrombopoietin (Tpo). Transduced primary human T-cells were incubated with the indicated concentrations of each drug and cells counted after three and five days FIG. 6—Enrichment kinetics of modular T-cell growth signal receptor engineered T-cells to varying concentrations of IL-2, Eltrombopag (Elt) or thrombopoietin (Tpo). Transduced primary human T-cells were diluted with non-transduced cells to a 20% transduction level. Cells were incubated with the indicated concentrations of each drug and the enrichment of each population established at the indicated time points by staining cells with anti-CD110-PE antibodies.

Figure 7:
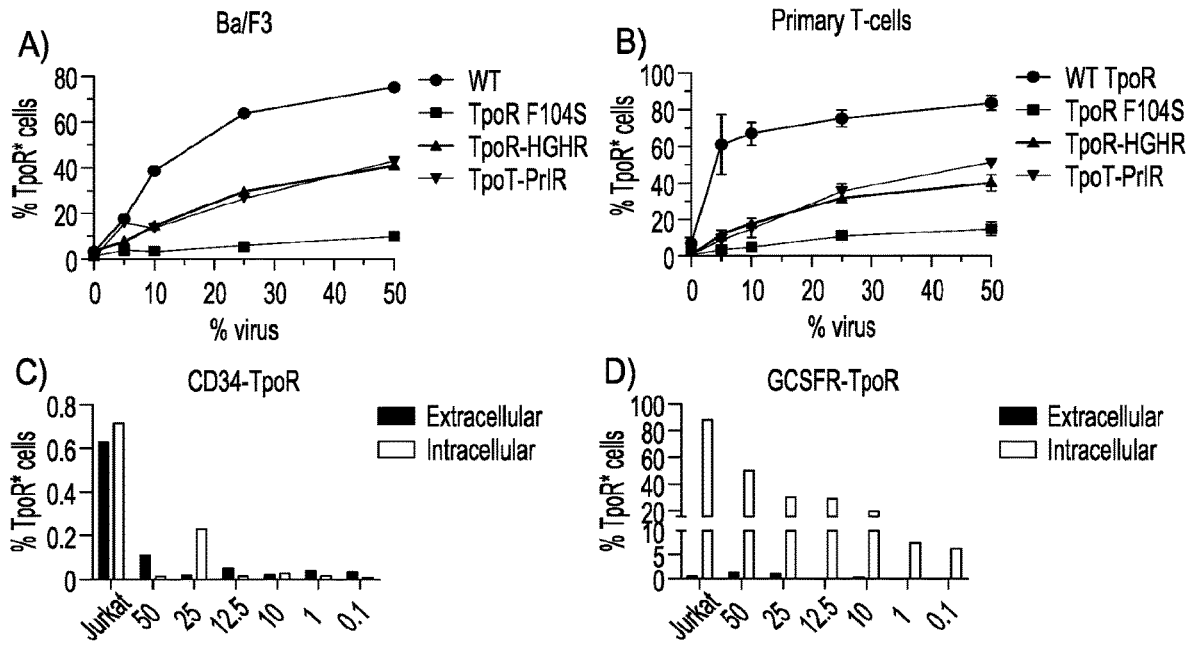

FIG. 7—Titration of lentiviral supernatants carrying genes for rGFR variants. Lentiviral supernatants were generated by transient transfection of 293T cells. Supernatants were added to Ba/F3 cells (A) and primary human T-cells (B) at the indicated concentrations. CD34-TpoR fusion (C) and TpoR-GCSFR (D) viral titration is shown extracellular and intracellular on Jurkat and primary human T-cells.

Figure 8:
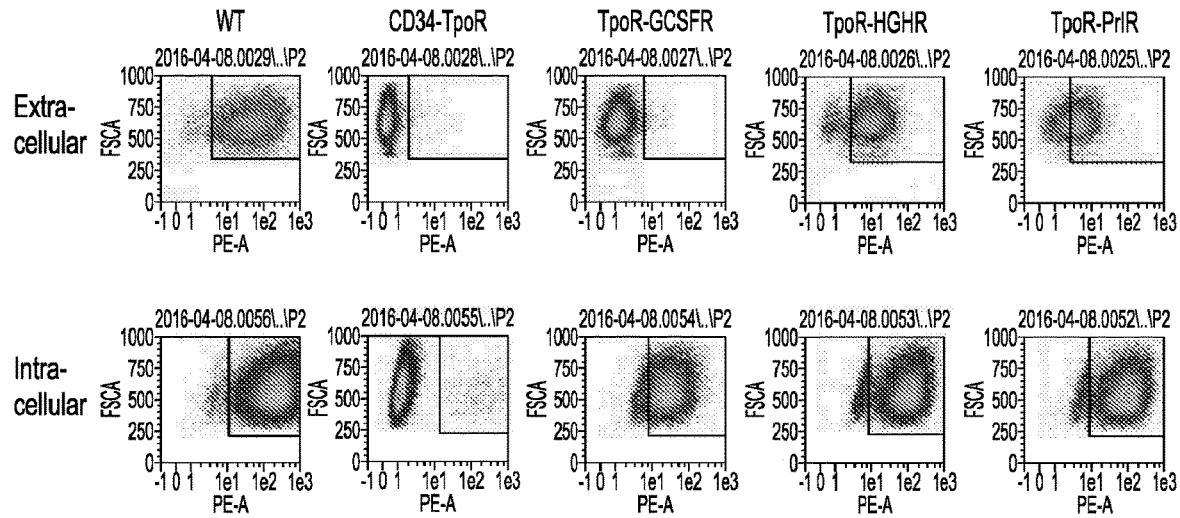

FIG. 8—Flow cytometry plots of rGFR in Jurkat T-cells. Lentiviral supernatants carrying genes for the indicated rGFR variants were added to Jurkat T-cells and expression determined after 3 days using PE conjugated anti-CD110 or anti-CD34 antibodies. Intracellular staining was performed using BD Cell Fixation/Permeabilisation Kit. Cells were analysed on a MACSQuant analyser.

Figure 9:
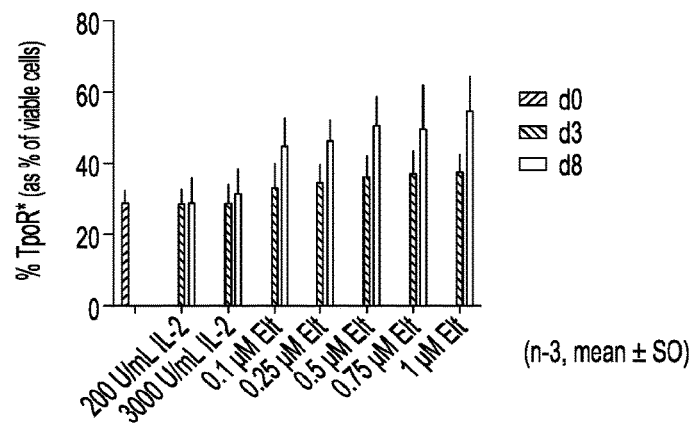

FIG. 9—Titration of Eltrombopag on primary human T-cells. Primary human T-cells from three donors were transduced with the WT TpoR and incubated in the presence of IL2 or Eltrombopag at the indicated concentrations. At day 3 and 8 cells were removed and the proportion of cells expressing the receptor assessed using PE conjugated anti-CD110 antibodies and a MACSQuant analyser.

Figure 10:
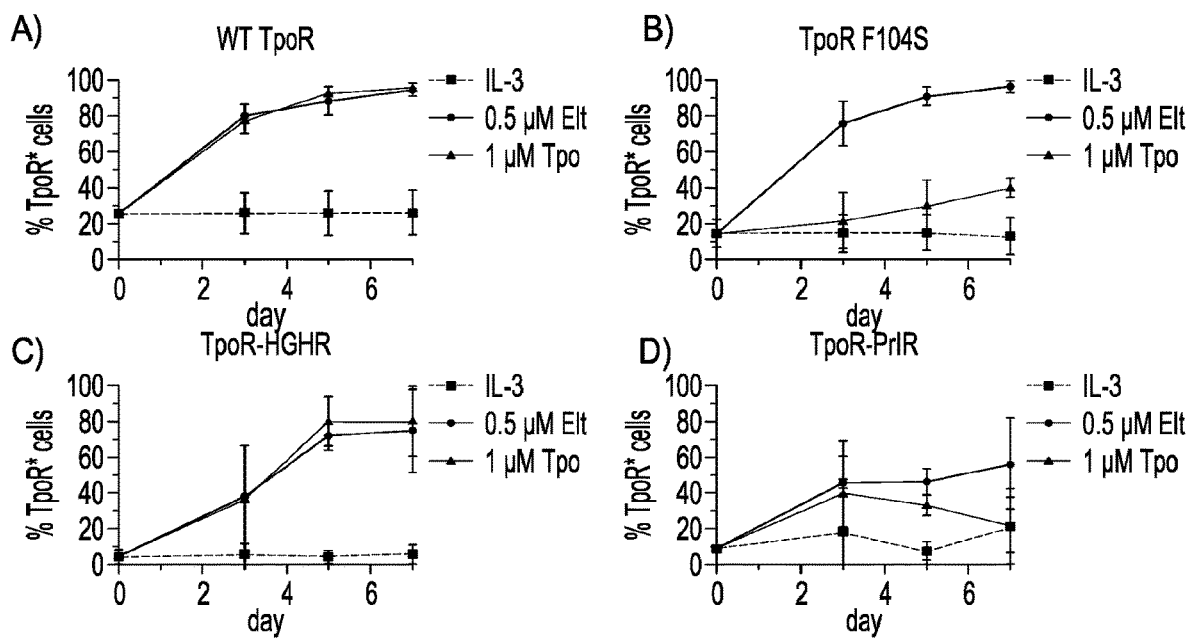

FIG. 10—Analysis of rGFR variants in Ba/F3 cells. The IL3 dependent cell line Ba/F3 was transduced with the indicated rGFR variants and incubated in the presence of 1 µM Tpo, 0.5 µM Eltrombopag or 0.5 ng/ml IL3. Cells were taken at days 3, 5 and 7 stained with PE conjugated anti-CD110 antibodies and analysed using a MACSQuant analyser.

Figure 11:
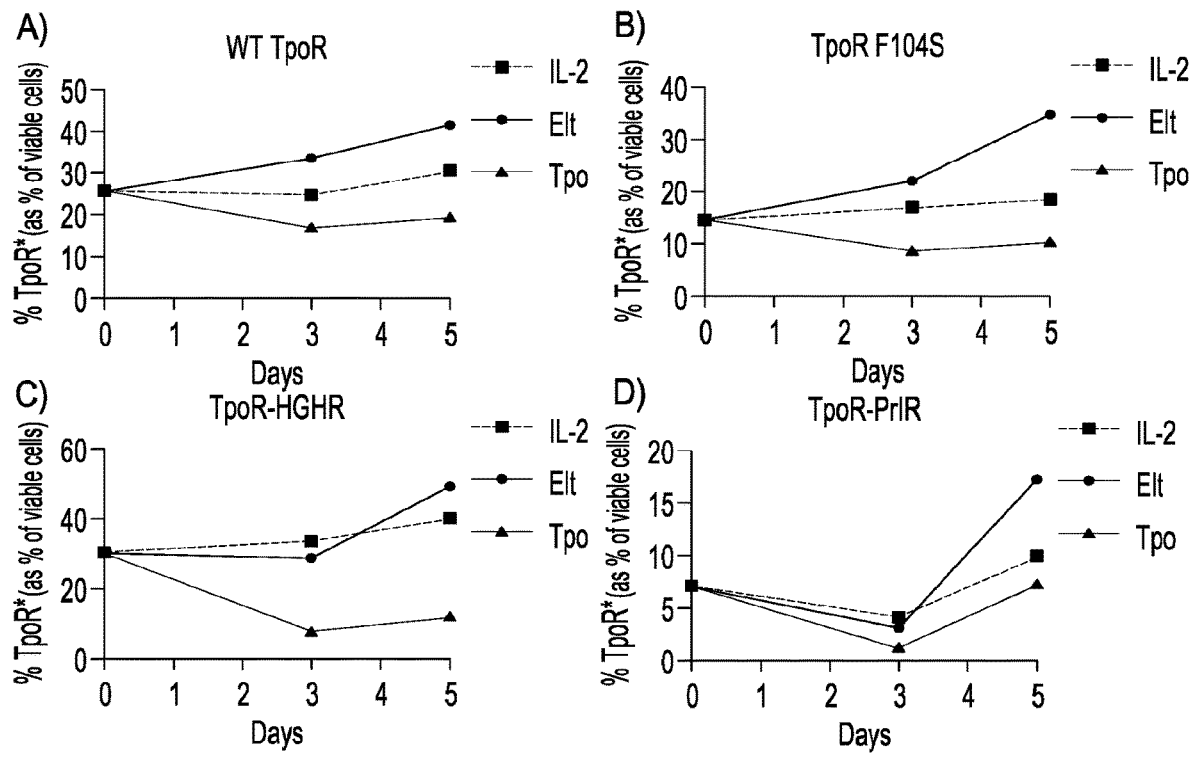

FIG. 11—Analysis of rGFR variants in primary human T-cells cells. Primary human T-cells from a healthy donor were transduced with the indicated rGFR variants and incubated in the presence of 1 µM Tpo, 0.5 µM Eltrombopag or 0.5 ng/ml IL3. Cells were taken at days 3 and 5 stained with PE conjugated anti-CD110 antibodies and analysed using a MACSQuant analyser.

Figure 12:
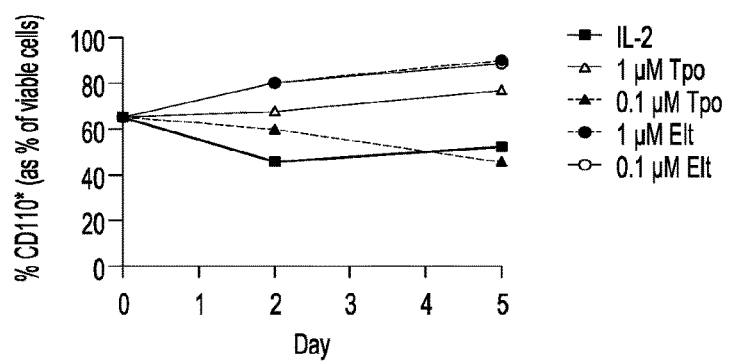

FIG. 12—Analysis of WT TpoR activity in Melanoma Tumour Infiltrating Lymphocytes. Tumour infiltrating lymphocytes (TIL) established from a cutaneous melanoma lesion were lentivirally transduced with the WT TpoR rGFR. The TIL were incubated in the presence of 200 IU/ml IL2 or the indicated concentrations of Tpo or Eltrombopag. At days 2 and 5 cells were removed, stained with PE conjugated anti-CD110 antibodies and analysed using a MACSQuant analyser.

Figure 13:
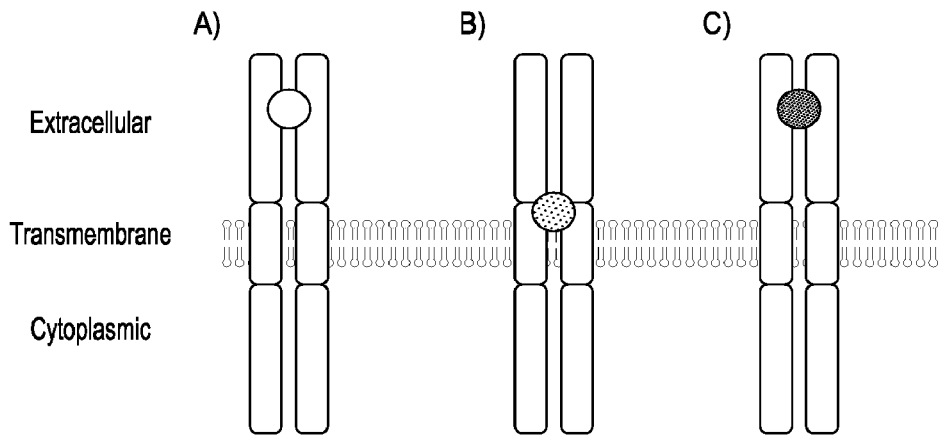

FIG. 13—is a schematic diagram showing a number of possible rGFR configurations.

(A) the native EC domain (such as TpoR EC domain) which binds growth factors (red) could be used to activate the receptor, (B) a drug which binds the TM domain (light grey) could be used, in which case the EC domain is redundant. The EC domain could then take the form of a marker gene such as truncated CD34 for selection and/or in vivo monitoring.

(C) the EC domain could be replaced with a receptor which allows controlled dimerization upon addition of a dimerising agent (Dark grey)

Figure 14:
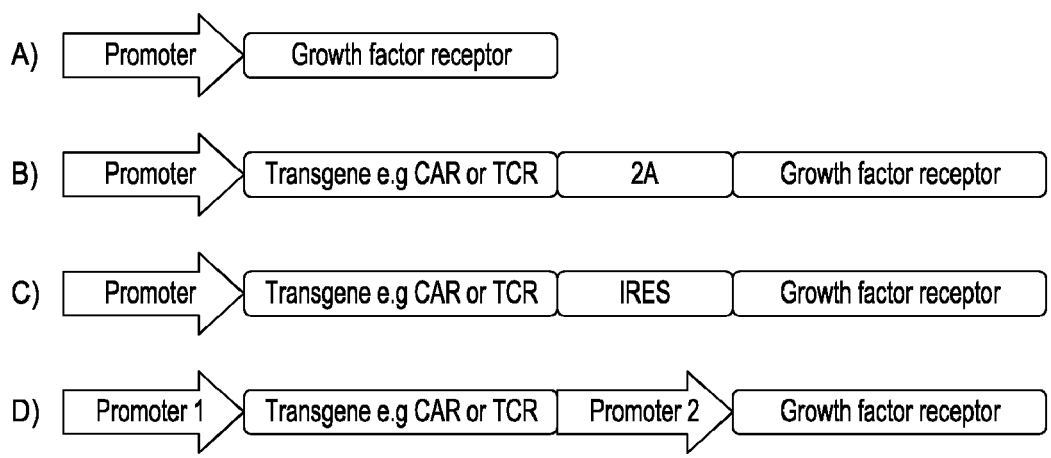

FIG. 14 is a schematic diagram showing a number of possible configurations of the nucleic acid constructs of the present invention.

A. The growth factor receptor may be expressed alone under the control of a promoter in a therapeutics population of cells, for example Tumour Infiltrating Lymphocytes B. The growth factor receptor may be expressed along with a therapeutics transgene such as a Chimeric Antigen Receptor (CAR) or T-cell Receptor (TCR) with the therapeutic transgene and growth factor receptor separated by a self cleaving polypeptide linker such as 2A C. The growth factor receptor may be expressed along with a therapeutics transgene such as a Chimeric Antigen Receptor (CAR) or T-cell Receptor (TCR) with the therapeutic transgene and growth factor receptor separated by an internal ribosome entry sequence (IRES)

D. The growth factor receptor may be expressed along with a therapeutic transgene such as a Chimeric Antigen Receptor (CAR) or T-cell Receptor (TCR).

Note: The position of the growth factor may be upstream (5') or downstream (3') of the therapeutic transgene when expressed from the same promoter. The therapeutic transgene and growth factor receptors may be under the control of separate promoters either on the same or different plasmids.

SUMMARY OF ASPECTS OF THE INVENTION

The present inventors have shown that it is possible to engineer lymphocytes, including T cells and NK cells that comprise a rGFR that can function as a growth switch. This allows the lymphocytes to be expanded in-vivo by administering the rGFR ligand to the patient. The inventors have shown that an rGFR, for example, based on the thrombopoietin (Tpo) receptor (TpoR; CD110, c-mpl), induces proliferation of the engineered lymphocyte following binding of an rGFR ligand to the receptor. Thus the ligand causes proliferation of cells that express the rGFR but is expected to have low toxicity due to the absence, or low expression, of receptors on other cells in the patient. rGFRs based on TpoR or other related growth factor receptors would be a valuable tool to augment lymphocyte expansion in vitro and in vivo for adoptive cell therapies.

Thus in a first aspect, the present invention provides a lymphocyte, including a T cell or NK cell, comprising a recombinant growth factor receptor (rGFR) comprising:

(i) an extracellular (EC) domain;
(ii) a thrombopoietin transmembrane (TM) domain; and
(iii) a growth factor receptor intracellular (IC) domain.

The rGFR is designed such that binding of the receptor ligand to the rGFR results in receptor activation and growth signalling to the cell to induce proliferation and/or survival. The rGFR may comprise the TM domain shown in SEQ ID No: 3 (also referred to herein as TpoR or human c-mpl TM domain) or a derivative or variant thereof that maintains signalling and cell proliferation in response to ligand binding.

The ligand may be human thrombopoietin, a thrombopoietin receptor agonist, e.g. Eltrombopag, or a tumour associated antigen.

The EC domain may be the human c-mpl EC domain (as shown in SEQ ID No: 2), which binds to human Tpo) or may be one or more of i) a truncated EC domain, ii) a truncated c-mpl EC domain, iii) a domain that binds to a tumour associated antigen, iv) an antibody or antibody fragment that binds to a tumour associated antigen; and v) a selection marker, for example CD34.

The IC domain of the rGFR may include a JAK binding domain. The IC domain may be from human growth hormone receptor, human prolactin receptor or the human thrombopoietin receptor (c-mpl).

The lymphocyte may be a T cell, including a Tumour Infiltrating Lymphocyte (TIL) a T Regulatory Cell (Treg) or a primary T cell, or an NK cell, or a dendritic cell.

In addition to the rGFR the lymphocyte, T or NK cell, may include a recombinant T-cell receptor (TCR) or Chimeric Antigen Receptor (CAR).

In a second aspect the invention provides a nucleic acid sequence encoding the rGFR.

In a third aspect the invention provides a vector which comprises a nucleic acid sequence according to the second aspect and, if present, a TCR and/or CAR nucleic acid sequence.

In a fourth aspect the invention provides a method for making a lymphocyte, or T or NK cell, according to the first aspect of the invention, which comprises the step of introducing a nucleic acid encoding the rGFR, or vector, into the lymphocyte.

In a fifth aspect the invention provides a pharmaceutical composition which comprises a vector according to the third aspect, or lymphocyte (including a T or NK cell) according to the first aspect, together with a pharmaceutically acceptable carrier, diluent or excipient.

In a sixth aspect the invention provides a method of in-vivo cell expansion comprising administering the lymphocytes, or T or NK cells, of the first aspect, or pharmaceutical composition of the fifth aspect to a subject. The cells may be expanded in-vivo by administering thrombopoietin, or a thrombopoietin agonist such as Eltrombopag, to a subject. Optionally, the cells may be expanded ex-vivo using a thrombopoietin, or a thrombopoietin agonist such as Eltrombopag prior to administration to the subject.

In a seventh aspect the invention provides a lymphocyte, including a T or NK cell, according to the first aspect, or vector according to the third aspect, for use in adoptive cell therapy.

In an eighth aspect the invention provides a lymphocyte, including a T or NK cell, according to the first aspect, or vector according to the third aspect, for use in a method of treating cancer.

In a ninth aspect the invention provides the use of a lymphocyte according to the first aspect, or the use of the vector according to the third aspect in the manufacture of a medicament for treating cancer.

In a tenth aspect the invention provides Eltrombopag or Tpo for use in adoptive cell therapy.

In an eleventh aspect the invention provides Eltrombopag or Tpo for use in the in-vivo or ex-vivo expansion of lymphocytes, including T or NK cells.

In a twelfth aspect the invention provides a lymphocyte, including T or NK cells, of the first aspect for use in combination with thrombopoietin or a thrombopoietin receptor agonist, for example Eltrombopag, in the treatment of a cancer.

In a further aspect there is provided a cell comprising a rGFR having an amino acid sequence with at least 80, 85, 90 or 95% identity to the amino acid sequence set out in SEQ ID No: 1, 5, 6, 7, 8, 9 or 10.

DETAILED DESCRIPTION

Recombinant Growth Factor Receptor (rGFR)

Provided herein are recombinant growth factor receptors (rGFR) comprising: (i) an extracellular (EC) domain; (ii) a thrombopoietin transmembrane (TM) domain; and (iii) a growth factor receptor intracellular (IC) domain. In a simple form the rGFR may be the full length of the human Tpo receptor (a codon optimised nucleic acid sequence of which is provided in FIG. 1 and SEQ ID No:11 herein and amino acid sequence in SEQ ID NO:1) or derivative or variant thereof that maintains signalling and cell proliferation, or cell survival, in response to ligand binding. The rGFR may be of modular form with the EC, TM and IC domains derived from different receptors. However, the rGFR must maintain its ability to transmit a growth signal to the cell upon ligand binding. The rGFR may be activated and transmit a growth signal to the cell upon ligand binding to the TM domain.

Suitable rGFRs may be selected based on GFRs with limited expression on normal human tissue, for example, GFRs that are expressed on only a small cell population or confined to a specific cell type, for example, c-kit. Alternatively, the native ligand binding domain of the growth factor receptor may be removed and e.g. replaced with a marker or other EC domain.

In some embodiments the rGFR comprises an EC domain comprising a ligand, such as an antibody or antibody fragment that binds to a tumour associated antigen, and a TM and IC domain from TpoR (c-mpl).

The rGFR may comprise an EC domain without growth factor binding function (for example a truncated form of the TpoR EC domain) and/or a marker, for example CD34), and the TM and IC domains from TpoR. Growth of cells carrying this type of receptor may then be stimulated by Eltrombopag binding to the TM domain.

There are a number of cytokine receptors with structural similarity to TpoR which could be used to generate novel chimeric GFRs. For example, the granulocyte colony stimulating factor receptor (GCSFR), human growth hormone receptor (HGHR) and prolactin receptor (PrlR) are all single chain and homodimeric making them ideal candidates for lentiviral gene transfer and subsequent T-cell surface expression.

The rGFR may comprise a TpoR EC and a TpoR TM domains with an IC domain from GCSFR, HGHR or PrlR.

In other embodiments, the rGFR may comprise a TpoR IC domain and a TpoR TM domain with an EC domain from CD34 (referred to herein as CD34-TpoR and shown in SEQ ID NO: 6). The CD34 EC domain may replace all, or a portion of, the TpoR EC domain.

In another embodiment, the rGFR is a TpoR containing an extracellular point mutation, F104S, for example, as shown in SEQ ID NO: 5, which has been shown to prevent responsiveness to Thrombopoietin but not Eltrombopag (Fox et al 2010).

The rGFR may be expressed alone under the control of a promoter in a therapeutic population of cells that have therapeutic activity, for example, Tumour Infiltrating Lymphocytes (TILs).

Alternatively, the GFR may be expressed along with a therapeutic transgene such as a Chimeric Antigen Receptor (CAR) and/or T-cell Receptor (TCR), for example as described in FIG. 14. Suitable TCRs and CARs are well known in the literature, for example HLA-A*02-NYESO-1 specific TCRs (Rapoport et al. Nat Med 2015) or anti-CD19scFv.CD3ζ fusion CARs (Kochenderfer et al. J Clin Oncol 2015) which have been successfully used to treat Myeloma or B-cell malignancies respectively. The rGFRs described herein may be expressed with any known CAR or TCR thus providing the cell with a regulatable growth switch to allow cell expansion in-vitro or in-vivo, and a conventional activation mechanism in the form of the TCR or CAR for anti-cancer activity. Thus the invention provides a cell for use in adoptive cell therapy comprising a rGFR as described herein and a TCR and/or CAR that specifically binds to a tumour associated antigen.

The rGFR may have the sequence shown as SEQ ID No: 1 or a variant thereof. The rGFR may have the TM domain (SEQ ID No: 3) and IC domain (SEQ ID No: 4) of the human Tpo receptor and a truncated Tpo receptor EC domain (without native ligand binding function).

The rGFR may have the sequence shown as SEQ ID No: 5, which is the human TpoR sequence having a F104S amino acid substitution.

The rGFR may have the sequence shown as SEQ ID No: 6 (also referred to herein as CD34-TpoR) or a variant thereof. As shown in SEQ ID No:6, amino acids 1 to 132 are the CD34 portion and amino acids 133 to 319 are from TpoR.

The rGFR may have the sequence shown as SEQ ID No: 7, which comprises the TpoR EC and TM domains with a GCSFR IC domain. For example, as shown in SEQ ID No: 7, amino acids 1 to 513 are the TpoR portion with amino acids 514-698 from GCSFR.

The rGFR may have the sequence shown as SEQ ID No: 8, (also referred to herein as TpoR-HGHR) or a variant thereof. As shown in SEQ ID No: 8, amino acids 1 to 513 are the TpoR portion with an IC domain (amino acids 514-863) from HGHR.

The rGFR may have the sequence shown as SEQ ID No: 9, (also referred to herein as TpoR-PrlR) or a variant thereof. As shown in SEQ ID No: 9, amino acids 1 to 513 are the TpoR portion with an IC domain (amino acids 514-877) from PrlR.

The rGFR may have the sequence shown as SEQ ID No: 10, (also referred to herein as TpoR-IL2RB) or a variant thereof. As shown in SEQ ID No: 10, amino acids 1 to 513 are the TpoR portion with an IC domain (amino acids 514-799) from IL2RB.

In embodiments there is provided a cell comprising an rGFR having at least 80, 85, 90 or 95% identity to the amino acid sequence set out in SEQ ID No: 1, 5, 6, 7, 8, 9 or 10

As will be apparent to the skilled person, the rGFRs as described herein are generally intended for expression in human cells, thus, typically, are constructed based on human sequences.

As will be apparent to the skilled person the rGFRs and cells comprising the rGFRS the described herein may be useful in any of the methods as described herein.

EC Domain

The EC domain may be the EC domain from TpoR (SEQ ID No: 2) or derivative or variant thereof that maintains signalling and cell proliferation, or in response to ligand binding to the receptor.

The EC domain may be a native EC domain which binds growth factors that could be used to activate the receptor.

The EC domain may not be required for rGFR signalling for example if TM domain is used that can cause receptor activation upon ligand binding e.g. the TpoR TM domain. The EC domain may then be a truncated native domain (e.g. without ligand binding function). For example, a truncated TpoR EC domain. The native EC domain may be replaced by a marker such as truncated CD34 for selection and/or in vivo monitoring.

The EC domain may be the TpoR EC domain having a F104S mutation. This mutation has been shown to prevent responsiveness to Thrombopoietin but not Eltrombopag (Fox et al 2010).

The EC domain may be replaced with a receptor which allows controlled dimerization upon addition of a dimerising agent, for example an EC domain comprising FKBP with rapamycin as a dimerising agent.

The EC domain may be different to the TM and IC domain. The EC domain may bind other ligands and could be antibody like allowing the growth factor receptor signalling domain to respond to a defined antigen. In this case a ligand binding-EC domain may be used to activate the receptor when it binds to its cognate molecule.

The EC domain may comprise an amino acid sequence from CD34, for example, as shown in SEQ ID No: 6.

TM Domain

The TM domain from the Tpo receptor (TpoR) as shown in SEQ ID No: 3 may be used, including a derivative or variant thereof that maintains signalling and cell proliferation or survival in response to ligand binding to the receptor. In some embodiments the TM domain may have at least 80, 85, 90 or 95% identity to the amino acid sequence set out in SEQ ID No: 3. This may be useful because TpoR is known to have limited expression in normal human tissues and it is also known to bind to Eltrombopag, thus an rGFR comprising a TM domain from the Tpo receptor can a be activated by exposing the cells in-vitro or in-vivo to a clinically validated compound with a known toxicity profile.

IC Domain

The growth factor receptor intracellular (IC) domain (shown in FIG. 1 and SEQ ID No: 4) from the Tpo receptor may be used including a derivative or variant thereof that maintains signalling and cell proliferation in response to ligand binding to the receptor. This may be combined with the TM domain from the Tpo receptor to achieve good levels of cell proliferation in response to ligand binding.

Other IC domains that are growth factor receptor like may be suitable for use in constructing the rGFRs of the present invention, as these receptors are known to activate the same cell signalling pathways as the Tpo receptor. For example, the IC domains from G-CSF, GM-CSF, prolactin, human growth hormone or IL2RB (see, for example, the IC domains of the rGFRs in SEQ ID No: 7, 8, 9 or 10) may be used to construct rGFRs when combined with the TpoR TM domain. The ability of an rGFR comprising these IC domains to induce cell proliferation or survival in response to a receptor agonist, for example, Eltrombopag, may then be determined using the methods described in the Examples herein.

Cells

The cells used in the present invention may be any lymphocyte that is useful in adoptive cell therapy, such as a T-cell or a natural killer (NK) cell, an NKT cell, a gamma/delta T-cell or T regulatory cell. The cells may be allogenic or autologous.

T cells or T lymphocytes are a type of lymphocyte that have a central role in cell-mediated immunity. They can be distinguished from other lymphocytes, such as B cells and natural killer cells (NK cells), by the presence of a T-cell receptor (TCR) on the cell surface. There are various types of T cell, as summarised below.

Cytolytic T cells (TC cells, or CTLs) destroy virally infected cells and tumor cells, and are also implicated in transplant rejection. CTLs express the CD8 molecule at their surface. These cells recognize their targets by binding to antigen associated with MHC class I, which is present on the surface of all nucleated cells. Through IL-10, adenosine and other molecules secreted by regulatory T cells, the CD8+ cells can be inactivated to an anergic state, which prevent autoimmune diseases such as experimental autoimmune encephalomyelitis.

Memory T cells are a subset of antigen-specific T cells that persist long-term after an infection has resolved. They quickly expand to large numbers of effector T cells upon re-exposure to their cognate antigen, thus providing the immune system with "memory" against past infections. Memory T cells comprise three subtypes: central memory T cells (TCM cells) and two types of effector memory T cells (TEM cells and TEM RA cells). Memory cells may be either CD4+ or CD8+. Memory T cells typically express the cell surface protein CD45RO.

Regulatory T cells (Treg cells), formerly known as suppressor T cells, are crucial for the maintenance of immunological tolerance. Their major role is to shut down T cell-mediated immunity toward the end of an immune reaction and to suppress auto-reactive T cells that escaped the process of negative selection in the thymus.

Two major classes of CD4+ Treg cells have been described—naturally occurring Treg cells and adaptive Treg cells.

Naturally occurring Treg cells (also known as CD4+ CD25+FoxP3+ Treg cells) arise in the thymus and have been linked to interactions between developing T cells with both myeloid (CD11c+) and plasmacytoid (CD123+) dendritic cells that have been activated with TSLP. Naturally occurring Treg cells can be distinguished from other T cells by the presence of an intracellular molecule called FoxP3.

Adaptive Treg cells (also known as Tr1 cells or Th3 cells) may originate during a normal immune response.

Natural Killer Cells (or NK cells) are a type of cytolytic cell which form part of the innate immune system. NK cells provide rapid responses to innate signals from virally infected cells in an MHC independent manner.

NK cells (belonging to the group of innate lymphoid cells) are defined as large granular lymphocytes (LGL) and constitute the third kind of cells differentiated from the common lymphoid progenitor generating B and T lymphocytes.

Tumour-infiltrating lymphocytes are white blood cells that have left the bloodstream and migrated into a tumour. They are mononuclear immune cells, a mix of different types of cells (i.e., T cells, B cells, NK cells, macrophages) in variable proportions, T cells being the most abundant cells. They can often be found in the stroma and within the tumour itself.

TILs are implicated in killing tumor cells. The presence of lymphocytes in tumours is often associated with better clinical outcomes.

Nucleic Acids

An aspect of the invention provides a nucleic acid sequence of the invention, encoding any of the rGFRs, polypeptides, or proteins described herein (including functional portions and functional variants thereof).

As used herein, the terms "polynucleotide", "nucleotide", and "nucleic acid" are intended to be synonymous with each other.

It will be understood by a skilled person that numerous different polynucleotides and nucleic acids can encode the same polypeptide as a result of the degeneracy of the genetic code. In addition, it is to be understood that skilled persons may, using routine techniques, make nucleotide substitutions that do not affect the polypeptide sequence encoded by the polynucleotides described here to reflect the codon usage of any particular host organism in which the polypeptides are to be expressed, e.g. codon optimisation.

Nucleic acids according to the invention may comprise DNA or RNA. They may be single-stranded or double-stranded. They may also be polynucleotides which include within them synthetic or modified nucleotides. A number of different types of modification to oligonucleotides are known in the art. These include methylphosphonate and phosphorothioate backbones, addition of acridine or polylysine chains at the 3' and/or 5' ends of the molecule. For the purposes of the present invention, it is to be understood that the polynucleotides may be modified by any method available in the art. Such modifications may be carried out in order to enhance the in vivo activity or life span of polynucleotides of interest.

The terms "variant", "homologue" or "derivative" in relation to a nucleotide sequence include any substitution of, variation of, modification of, replacement of, deletion of or addition of one (or more) nucleic acid from or to the sequence.

The nucleic acid sequence may encode the protein sequence shown as SEQ ID No. 1 or a variant thereof, including a nucleic acid sequence encoding a truncated form of the Tpo receptor which has lacks the last five amino acids of the wild type Tpo receptor and thus has a truncated IC domain.

The nucleotide sequence may comprise the codon optimised human TpoR nucleic acid sequence shown in FIG. 1 or variants thereof.

The invention also provides a nucleic acid sequence which comprises a nucleic acid sequence encoding a rGFR and a further nucleic acid sequence encoding a T-cell receptor (TCR) and/or chimeric antigen receptor (CAR).

The nucleic acid sequences may be joined by a sequence allowing co-expression of the two or more nucleic acid sequences. For example, the construct may comprise an internal promoter, an internal ribosome entry sequence (IRES) sequence or a sequence encoding a cleavage site. The cleavage site may be self-cleaving, such that when the polypeptide is produced, it is immediately cleaved into the discrete proteins without the need for any external cleavage activity.

Various self-cleaving sites are known, including the Foot-and-Mouth disease virus (FMDV) and the 2a self-cleaving peptide.

The co-expressing sequence may be an internal ribosome entry sequence (IRES). The co-expressing sequence may be an internal promoter.

Vectors

In an aspect, the present invention provides a vector which comprises a nucleic acid sequence or nucleic acid construct of the invention.

Such a vector may be used to introduce the nucleic acid sequence(s) or nucleic acid construct(s) into a host cell so that it expresses one or more rGFR(s) according to the first aspect of the invention and, optionally, one or more other proteins of interest (POI), for example a TCR or a CAR.

The vector may, for example, be a plasmid or a viral vector, such as a retroviral vector or a lentiviral vector, or a transposon based vector or synthetic mRNA. Vectors derived from retroviruses, such as the lentivirus, are suitable tools to achieve long-term gene transfer since they allow long-term, stable integration of a transgene or transgenes and its propagation in daughter cells.

The vector may be capable of transfecting or transducing a lymphocyte including a T cell or an NK cell.

The present invention also provides vectors in which a nucleic acid of the present invention is inserted.

The expression of natural or synthetic nucleic acids encoding a rGFR, and optionally a TCR or CAR is typically achieved by operably linking a nucleic acid encoding the rGFR and TCR/CAR polypeptide or portions thereof to one or more promoters, and incorporating the construct into an expression vector. The vectors can be suitable for replication and integration in eukaryotic cells. Typical cloning vectors contain transcription and translation terminators, initiation sequences, and promoters useful for regulation of the expression of the desired nucleic acid sequence.

Viral vector technology is well known in the art and is described, for example, in Sambrook et al. (2001, Molecular Cloning: A Laboratory Manual, Cold Spring Harbor Laboratory, New York), and in other virology and molecular biology manuals, see also, WO 01/96584; WO 01/29058; and U.S. Pat. No. 6,326,193).

In some embodiments, the nucleic acid constructs are as shown in FIG. 14. In some embodiments the nucleic acids are multicystronic constructs that permit the expression of multiple transgenes (e.g., rGFR and a TCR and/or CAR etc.) under the control of a single promoter. In some embodiments, the transgenes (e.g., rGFR and a TCR and/or CAR etc.) are separated by a self-cleaving 2A peptide. Examples of 2A peptides useful in the nucleic acid constructs of the invention include F2A, P2A, T2A and E2A. In other embodiments of the invention, the nucleic acid construct of the invention is a multicystronic construct comprising two promoters; one promoter driving the expression of rGFR and the other promoter driving the expression of the TCR or CAR. In some embodiments, the dual promoter constructs of the invention are uni-directional. In other embodiments, the dual promoter constructs of the invention are bi-directional.

In order to assess the expression of the rGFR polypeptide or portions thereof, the expression vector to be introduced into a cell can also contain either a selectable marker gene or a reporter gene or both to facilitate identification and selection of expressing cells from the population of cells sought to be transfected or transduced through viral vectors.

The rGFR polypeptide may incorporate a marker, such as CD34, as part of the EC domain.

Pharmaceutical Composition

The present invention also relates to a pharmaceutical composition containing a vector or a rGFR expressing cell of the invention together with a pharmaceutically acceptable carrier, diluent or excipient, and optionally one or more further pharmaceutically active polypeptides and/or compounds. Such a formulation may, for example, be in a form suitable for intravenous infusion.

Method of Treatment

Cells, including T and NK cells, expressing rGFRs for use in the methods of the present may either be created ex vivo either from a patient's own peripheral blood (autologous), or in the setting of a haematopoietic stem cell transplant from donor peripheral blood (allogenic), or peripheral blood from an unconnected donor (allogenic). The cells may be tumour infiltrating lymphocytes (TILs). Alternatively, T-cells or NK cells may be derived from ex-vivo differentiation of inducible progenitor cells or embryonic progenitor cells to T-cells or NK cells. In these instances, T-cells expressing a rGFR and, optionally, a CAR and/or TCR, are generated by introducing DNA or RNA coding for the rGFR and, optionally, a CAR and/or TCR, by one of many means including transduction with a viral vector, transfection with DNA or RNA.

T or NK cells expressing a rGFR of the present invention and, optionally, expressing a TCR and/or CAR may be used for the treatment of haemotological cancers or solid tumours.

A method for the treatment of disease relates to the therapeutic use of a vector or cell, including a T or NK cell, of the invention. In this respect, the vector, or T or NK cell may be administered to a subject having an existing disease or condition in order to lessen, reduce or improve at least one symptom associated with the disease and/or to slow down, reduce or block the progression of the disease. The method of the invention may cause or promote T-cell mediated killing of cancer cells.

The vector, or T or NK cell according to the present invention may be administered to a patient with one or more additional therapeutic agents. The one or more additional therapeutic agents can be coadministered to the patient. By "coadministering" is meant administering one or more additional therapeutic agents and the vector, or T or NK cell of the present invention sufficiently close in time such that the vector, or T or NK cell can enhance the effect of one or more additional therapeutic agents, or vice versa. In this regard, the vectors or cells can be administered first and the one or more additional therapeutic agents can be administered second, or vice versa. Alternatively, the vectors or cells and the one or more additional therapeutic agents can be administered simultaneously. Suitable therapeutic agents that may be co-administered with the vectors or cells of the present invention include any growth factor receptor agonist that activates the rGFR, for example, Eltrombopag (rINN, code-named SB-497115-GR) or Romiplostim.

Eltrombopag may be particularly useful in the methods of the invention as its toxicity profile is known. In preclinical studies, the compound was shown to interact selectively with the thrombopoietin receptor, leading to activation of the JAK-STAT signalling pathway and increased proliferation and differentiation of megakaryocytes. Animal studies confirmed that administration could increase platelet counts. In 73 healthy volunteers, higher doses of Eltrombopag caused larger increases in the number of circulating platelets without tolerability problems, see, for example, Jenkins J M, Williams D, Deng Y, Uhl J, Kitchen V, Collins D, Erickson-Miller CL (June 2007). "Phase 1 clinical study of eltrombopag, an oral, nonpeptide thrombopoietin receptor agonist". Blood 109 (11): 4739-41. Thus in the methods of the invention suitable dosages of Eltrombopag may be determined based on previously published clinical studies and the in-vitro assays described herein.

Another agent that may be useful is IL-2, as this is currently used in existing cell therapies to boost the activity of administered cells. However, as stated earlier, IL-2 treatment is associated with toxicity and tolerability issues. Thus it is an aim of present invention to stimulate cell proliferation using an agonist that binds to the rGFR and, therefore, reduce the amount of IL-2 that must be administered (e.g. to levels that are less toxic) or even eliminate the need for IL-2 administration.

For purposes of the inventive methods, wherein cells are administered to the patient, the cells can be cells that are allogeneic or autologous to the patient.

Various further aspects and embodiments of the present invention will be apparent to those skilled in the art in view of the present disclosure.

All documents mentioned in this specification are incorporated herein by reference in their entirety.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

Certain aspects and embodiments of the invention will now be illustrated by way of example and with reference to the figures described above and tables described below.

EXAMPLES

Example 1—Production of T-Cells Expressing rGFR

Materials and Methods

Construct design—The entire human TpoR nucleic acid sequence, or mutant truncated variant lacking the final five N-terminal amino acids and described in Saka et al. 2013 The constructs were cloned into pSF.Lenti (Oxford Genetics) via an XbaI and NheI site. The CD34 fusion receptor was generated by fusing the extracellular domain of CD34 directly to the transmembrane and cytoplasmic domain of the human TpoR. The HGHR, PrlR and GCSFR fusions were generated by fusing the HGHR, PrlR or GCSFR cytoplasmic domains respectively directly to the extracellular and transmembrane domain of the TpoR. The F104S mutant was generated by cloning in a fragment of the TpoR via XbaI and XhoI restriction sites. All fragments and constructs were codon optimised and gene synthesised by Genewiz.

Lentiviral Production—Lentiviral production was performed using a three-plasmid packaging system (Cell Biolabs, San Diego, USA) by mixing 10 µg of each plasmid, plus 10 µg of the pSF.Lenti lentiviral plasmid containing the transgene, together in serum free RPMI containing 50 mM $CaCl_2$. The mixture was added dropwise to a 50% confluent monolayer of 293T cells in 75 cm2 flasks. The viral supernatants were collected at 48 and 72 h post transfection, pooled and concentrated using LentiPac lentiviral supernatant concentration (GeneCopoeia, Rockville, Maryland, USA) solution according to the manufacturer's instructions. Lentiviral supernatants were concentrated 10-fold and used to directly infect primary human T-cells in the presence of 4 µg/ml polybrene (Sigma-Aldrich, Dorset, UK).

Peripheral blood mononuclear cells were isolated from normal healthy donors before activation for 24 hours with T-cell activation and expansion beads (Invitrogen) according to the manufacturer's instructions before addition of lentiviral supernatants.

Following expansion cells were washed excessively to remove any exogenous IL2 and plated into 96-well U-bottom plates. Cells were supplemented with IL2 (Proleukin), recombinant human Tpo (Miltenyi Biotec) or Eltrombopag (Stratech Scientific, Suffolk, UK). At various time points thereafter cells were either stained with a 1:400 dilution of eFlor-450 fixable viability dye (eBioscience, UK) and counted directly from the wells using a MACSQuant Cytometer, or were stained with viability dye plus phycoerythrin conjugated anti-CD110 antibodies (Miltenyi Biotec, UK) and analysed using a MACSQuant cytomter. Cell viability and/or transduction level was then analysed using MACSQuantify software (Miltenyi Biotec, UK).

RESULTS—Primary human T-cells were isolated from Buffy coats obtained from the NHSBT. T-cells were isolated by Ficoll-mediated isolation. The isolated T-cells were activated with human T-cell activation and expansion beads. Cells were incubated with concentrated lentiviral particles and expanded over a number of days. The lentivirus contained the DNA sequence of full length human TpoR or a truncated variant thereof lacking the final five aa which has previously been demonstrated to enhance the growth responsiveness of haematopoietic stem cells to Tpo (Saks et al. 2013), under the control of an EF1α promoter (FIGS. 1 & 2). Following expansion transduction levels were assessed by directly staining for the TpoR protein using anti-CD110 antibodies. FIG. 4 shows transduction efficiency of WT and mt TpoR variants in primary human T-cells compared with non-transduced cells. Transduction efficiencies of >90% could be achieved whereas non-transduced cells were 5% positive for TpoR.

Initially WT transduced cells with a transduction level of 94% were plated at $5\times10^4$ cells/well in 96-well U-bottom plates and incubated with varying concentrations of IL-2, Eltrombopag or Tpo. After three and five days the cells were stained with EFlor-450 Live/dead fixable viability dye and the cells in each well counted by flow cytometry. FIG. 5 demonstrates dose dependent responses in relative increase of cell number as the concentration of each compound increases. It appears however that responses to Eltrombopag are maximal at around 0.1 µM with concentrations above this becoming toxic. We did not see maximal responses to Tpo comparable to those seen with Eltrombopag or IL-2, possibly as optimal concentrations were not used.

Figure 6:
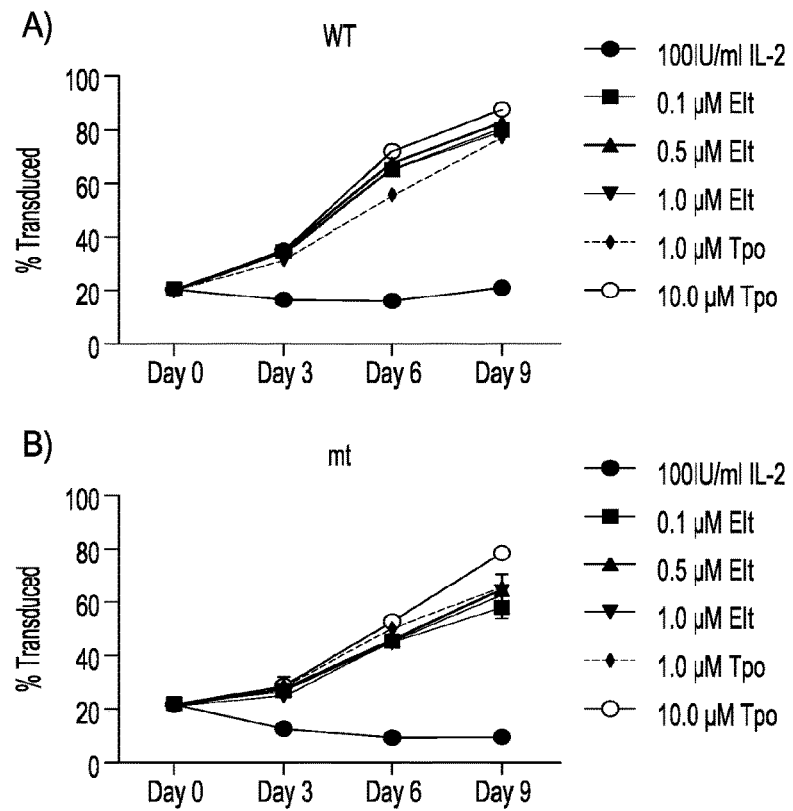

Additional cells were diluted with non-transduced cells to achieve a population with 20% transduction efficiency. The T-cells were incubated with 100 IU/ml IL-2; 0.1, 0.5 or 1.0 µg/ml Eltrombopag; or 1.0 or 10.0 µg/ml recombinant human Tpo. After three, six and nine days the cells were stained with anti-CD110 (TpoR) antibodies and analysed by flow cytometry. Cells harbouring either the WT or mt TpoR responded to Eltrombopag or Tpo and the populations gradually became enriched over the course of the experiment. The responsiveness of cells harbouring the WT receptor was above and beyond that of cells harbouring the mt receptor. 0.5 µM Eltrombopag stimulated cells enriched to 83.5% TpoR positive whereas mt cells enriched to 66.6% positive under the same conditions. In the presence of 10.0 µM Tpo WT cells enriched to 87.5% whereas mt enriched to 77.9% positive. In both cases cells stimulated with IL-2 alone did not become enriched over time (FIG. 6).

There are a number of cytokine receptors with structural similarity to TpoR which could be used to generate novel chimeric GFRs. For example, the granulocyte colony stimulating factor receptor (GCSFR), Human growth hormone receptor (HGHR) and prolactin receptor (PrlR) are all single chain and homodimeric making them ideal candidates for lentiviral gene transfer and subsequent T-cell surface expression. We therefore constructed several variations on the existing WT TpoR by replacing the intracellular domain of the TpoR with those obtained from GCSFR, HGHR or PrlR. Additionally we also created two other variants:
i) TpoR with the extracellular domain obtained from CD34 (CD34-TpoR); ii) TpoR F104S containing an extracellular point mutation which has been shown to prevent responsiveness to Thrombopoietin but not Eltrombopag (Fox et al 2010).

Lentiviral supernatants were made from each of the new variant plasmid constructs and used to directly infect the IL-3 dependent murine B-cell line Ba/F3 and primary human T-cells (FIGS. 7A & B). The WT receptor was the most efficiently expressed variant in both Ba/F3 and human T-cells. The F104S mutation appeared to negatively impact on viral titres, although it still expressed at a level sufficient for experiments to be performed. The HGHR and PrlR variants both expressed to sufficient levels too. Two of the receptors tested failed to express to levels sufficient to perform subsequent experiments. The TpoR-GCSFR fusion receptor could not be detected on the surface of transduced Jurkat cells or primary human T-cells but was expressed readily upon intracellular staining suggesting that there was issues with this receptor being transported to the plasma membrane (FIG. 8). The CD34-TpoR fusion showed limited surface expression in Jurkat cells although could be detected as a clear but small population intracellularly using an anti-CD34 antibody (FIG. 8). The most likely explanation is that this receptor generates very low titre viral particles.

Initial experiments with the WT receptor used a wide range of Eltrombopag concentrations. We therefore conducted an initial experiment using WT TpoR engineered T-cells to determine a more precise concentration or range of concentrations to use for successive experiments. (FIG. 9). There was very little difference in the enrichment of TpoR+ cells over 3 and 8 days with varying concentrations of Eltrombopag, we therefore chose 0.5 µM as an optimal concentration for further experiments.

To determine whether the new variants generated were functionally active we transduced the IL3 dependent cell line Ba/F3 and incubated the cells with either IL-3, 0.5 µM Eltrombopag or 1.0 µM Tpo and measured the proportion of cells expressing the indicated TpoR at days 3, 5 and 7. As expected the WT TpoR was able to support the enrichment of transduced cells in the presence of Eltrombopag and Tpo, the mutant F104S variant which does not bind Tpo was also able to support the enrichment of transduced cells in the presence of Eltrombopag but, as expected, had much reduced activity in response to Tpo. The TpoR-HGHR and TpoR-PrlR variants also showed functional activity in response to Eltrombopag and Tpo; however, the TpoR-PrlR variant appeared relatively unstable on the cell surface (FIG. 10) and showed less robust responses to Eltrombopag and Tpo compared with the other variants.

The WT, F104S, HGHR and PrlR variants were then tested for functional activity in primary human T-cells. Eltrombopag, but not Tpo nor IL-2, induced preferential enrichment of WT and F104S TpoR+ T-cells. Both the TpoR-HGHR and TpoR-PrlR variants also demonstrated Eltrombopag induced enrichment but the effect was not as pronounced as compared to WT or F104S (FIG. 11).

Next we aimed to determine whether the WT TpoR was functionally active in Tumour Infiltrating Lymphocytes (TIL). It was possible that the high doses of IL2 used to generate TIL cultures could make them more dependent on IL2 for subsequent growth. To this end we added lentiviral supernatants to melanoma TIL cultures. Cells were transduced to 65% (FIG. 12). The TILs were cultured in the presence of 200 IU/ml IL-2, or Eltrombopag or Tpo. Cells were analysed for TpoR expression at days 2 and 5. High (1 µM) but not low (0.1 µM) Tpo was able to induce enrichment of TpoR+ T-cells over the seven day period of the experiment. Moreover, both low (0.1 µM) and high (1.0 µM) dose Eltrombopag was able to induce enrichment (65% to 89% and 65% to 90% TpoR+). In contrast there was no enrichment of TpoR+ cells in the presence of IL2 supporting the notion that this is driven by signals through the TpoR.

CONCLUSION

Growth factor receptors responsive to clinically available drugs can be transferred to T-cells by gene transfer technology and therein maintain their functional capacity to deliver cell growth/survival signals. Importantly we show that as an example, TpoR engrafted primary human T-cells respond to the clinically available drug Eltrombopag and expand and survive in the absence of IL-2 which is normally required for optimal T-cell growth. The responses to Eltrombopag were not as great as those seen towards IL-2; however, there are a number of potential avenues that can be explored to optimise the growth responses. Here we initially test a truncated TpoR previously shown to enhance the responsiveness of haematopoietic stem cells to TpoR engagement (Saka et al. 2013). We show that this truncated mutant receptor was not as efficient at inducing cell growth as the WT in T-cells.

Here we tested a number of functional variants; i) an F104S extracellular mutant variant which has been previously shown to be unresponsive to Tpo; ii) a variant where the extracellular domain is replaced with human CD34; iii) three variants in which the intracellular domain is swapped for either the human growth hormone receptor (HGHR), the prolactin receptor (PrlR) or granulocyte colony stimulating factor (GCSFR). As predicted the F104S variant reduced responsiveness to Tpo, this is an important observation as it means that this variant could be safer as engineered cells would not be able to proliferate in response to circulating natural levels of Tpo but retain responsiveness to Eltrombopag. The CD34 variant expressed, however, there were some issues with viral titre which need to be resolved. Two of the three cytoplasmic domain variants functioned well (the GCSFR not expressing at the cell surface), although they showed relatively equivalent responsiveness to Eltrombopag as the WT receptor. Importantly the variants have shown how the WT receptor can be modified in attempts to improve activity.

We also demonstrate that the growth factor receptor retains activity in Tumour Infiltrating Lymphocytes (TIL).

TIL are routinely grown out in the presence of very high concentrations of IL2 (up to 6000 IU/ml in some cases) and so there was a worry that these cells would be acutely dependent on IL2 for subsequent survival. Here we show that rGFR engineered TIL can be readily enriched in the presence of Eltrombopag. This opens up the possibility of using a rGFR based on the WT TpoR to engineer TIL to survive in vivo in the absence of exogenously administered IL2.

REFERENCES

Columbyova L, Loda M, Scadden D T. Cancer Res. 1995 Aug. 15; 55(16):3509-12. Thrombopoietin receptor expression in human cancer cell lines and primary tissues.

Grupp S A, Kalos M, Barrett D, Aplenc R, Porter D L, Rheingold S R, Teachey D T, Chew A, Hauck B, Wright J F, Milone M C, Levine B L, June C H. N Engl J Med. 2013 Apr. 18; 368(16):1509-18. Chimeric antigen receptor-modified T cells for acute lymphoid leukemia.

Erickson-Miller C L, Delorme E, Tian S S, Hopson C B, Landis A J, Valoret E I, Sellers T S, Rosen J, Miller S G, Luengo J I, Duffy K J, Jenkins J M. Stem Cells. 2009 February; 27(2):424-30. Preclinical activity of eltrombopag (SB-497115), an oral, nonpeptide thrombopoietin receptor agonist.

Fox N E, Lim J, Chen R, Geddis A E. Exp Hematol. 2010 May; 38(5):384-91. F104S c-Mpl responds to a transmembrane domain-binding thrombopoietin receptor agonist: proof of concept that selected receptor mutations in congenital amegakaryocytic thrombocytopenia can be stimulated with alternative thrombopoietic agents.

Kawahara M, Kimura H, Ueda H, Nagamune T. Biochem Biophys Res Commun. 2004 Feb. 27; 315(1):132-8. Selection of genetically modified cell population using hapten-specific antibody/receptor chimera.

Kochenderfer J N, Dudley M E, Kassim S H, Somerville R P, Carpenter R O, Stetler-Stevenson M, Yang J C, Phan G Q, Hughes M S, Sherry R M, Raffeld M, Feldman S, Lu L, Li Y F, Ngo L T, Goy A, Feldman T, Spaner D E, Wang M L, Chen C C, Kranick S M, Nath A, Nathan D A, Morton K E, Toomey M A, Rosenberg S A. J Clin Oncol. 2015 33(6):540-9. Chemotherapy-refractory diffuse large B-cell lymphoma and indolent B-cell malignancies can be effectively treated with autologous T cells expressing an anti-CD19 chimeric antigen receptor.

Jin L, Zeng H, Chien S, Otto K G, Richard R E, Emery D W, Blau C A. Nat Genet. 2000 September; 26(1):64-6. In vivo selection using a cell-growth switch.

Kawahara M, Chen J, Sogo T, Teng J, Otsu M, Onodera M, Nakauchi H, Ueda H, Nagamune T. Cytokine. 2011 September; 55(3):402-8. Growth promotion of genetically modified hematopoietic progenitors using an antibody/c-Mpl chimera.

Morgan R A, Dudley M E, Wunderlich J R, Hughes M S, Yang J C, Sherry R M, Royal R E, Topalian S L, Kammula U S, Restifo N P, Zheng Z, Nahvi A, de Vries C R, Rogers-Freezer L J, Mavroukakis S A, Rosenberg S A. Science. 2006 Oct. 6; 314(5796):126-9. Cancer regression in patients after transfer of genetically engineered lymphocytes.

Nagashima T, Ueda Y, Hanazono Y, Kume A, Shibata H, Ageyama N, Terao K, Ozawa K, Hasegawa M. J Gene Med. 2004 January; 6(1):22-31. In vivo expansion of gene-modified hematopoietic cells by a novel selective amplifier gene utilizing the erythropoietin receptor as a molecular switch.

Rapoport A P, Stadtmauer E A, Binder-Scholl G K, Goloubeva O, Vogl D T, Lacey S F, Badros A Z, Garfall A, Weiss B, Finklestein J, Kulikovskaya I, Sinha S K, Kronsberg S, Gupta M, Bond S, Melchiori L, Brewer J E, Bennett A D, Gerry A B, Pumphrey N J, Williams D, Tayton-Martin H K, Ribeiro L, Holdich T, Yanovich S, Hardy N, Yared J, Kerr N, Philip S, Westphal S, Siegel D L, Levine B L, Jakobsen B K, Kalos M, June C H. Nat Med. 2015 August; 21(8):914-21. NY-ESO-1-specific TCR-engineered T cells mediate sustained antigen-specific antitumor effects in myeloma.

Richard R E, Wood B, Zeng H, Jin L, Papayannopoulou T, Blau C A. Blood. 2000 Jan. 15; 95(2):430-6. Expansion of genetically modified primary human hemopoietic cells using chemical inducers of dimerization.

Rosenberg S A, Yang J C, Sherry R M, Kammula U S, Hughes M S, Phan G Q, Citrin D E, Restifo N P, Robbins P F, Wunderlich J R, Morton K E, Laurencot C M, Steinberg S M, White D E, Dudley M E. Clin Cancer Res. 2011 Jul. 1; 17(13):4550-7. Durable complete responses in heavily pretreated patients with metastatic melanoma using T-cell transfer immunotherapy.

Saka K, Kawahara M, Teng J, Otsu M, Nakauchi H, Nagamune T. J Biotechnol. 2013 December; 168(4):659-65. Top-down motif engineering of a cytokine receptor for directing ex vivo expansion of hematopoietic stem cells.

Saka K, Kawahara M, Ueda H, Nagamune T. Biotechnol Bioeng. 2012 June; 109(6):1528-37. Activation of target signal transducers utilizing chimeric receptors with signaling-molecule binding motifs.

Yamane N, Tanaka Y, Ohyabu N, Yamane S, Maekawa K, Ishizaki J, Suzuki R, Itoh T, Takemoto H. Eur J Pharmacol. 2008 May 31; 586(1-3):44-51. Characterization of novel non-peptide thrombopoietin mimetics, their species specificity and the activation mechanism of the thrombopoietin receptor.

The invention claimed is:

1. A method of cell expansion of a T or natural killer (NK) cell comprising, contacting the T or NK cell with a ligand; wherein the T or NK cell comprises a recombinant thrombopoietin receptor (TpoR) comprising:

(i) a thrombopoietin receptor extracellular (EC) domain, (ii) a thrombopoietin receptor transmembrane (TM) domain, and (iii) an intracellular (IC) domain, wherein the IC domain is from a human growth hormone receptor or a human prolactin receptor;
wherein the ligand binds to the TpoR; and
wherein the method does not comprise contacting the T or NK cell with exogenous IL-2.

2. The method of claim 1, wherein binding of the ligand to the TpoR induces proliferation of the T or NK cell in the absence of exogenous IL-2.

3. The method of claim 2, wherein the ligand is human thrombopoietin or a thrombopoietin receptor agonist.

4. The method of claim 3, wherein the thrombopoietin receptor agonist binds to the TM domain.

5. The method of claim 4, wherein the thrombopoietin receptor agonist is selected from Eltrombopag or Romiplostim.

6. The method of claim 1, wherein the TpoR has a TM sequence of SEQ ID NO: 3 or a variant thereof having at least 95% sequence identity to SEQ ID NO: 3 which binds a thrombopoietin receptor agonist.

7. The method of claim 1, wherein the IC domain comprises the sequence according to amino acids 514-863 of SEQ ID NO: 8.

8. The method of claim 1, wherein the TM domain comprises the sequence of SEQ ID NO: 3 or a variant thereof having at least 95% sequence identity to SEQ ID NO: 3, and
wherein the IC domain comprises the sequence according to amino acids 514-863 of SEQ ID NO: 8.

9. The method of claim 1, wherein the TpoR comprises the sequence of SEQ ID NO: 8 or 9, or a variant thereof having at least 95% sequence identity to SEQ ID NO: 8 or 9 but retains the capacity to i) bind to human thrombopoietin or a human thrombopoietin receptor agonist and ii) induce cell proliferation or survival.

10. The method of claim 1, wherein the EC domain does not have a growth factor binding function and the TM domain binds to Eltrombopag.

11. The method of claim 1, wherein the T cell is selected from a Tumour Infiltrating Lymphocyte (TIL), a T Regulatory Cell (Treg) or a primary T cell.

12. The method of claim 1, wherein the T or NK cell further comprises a recombinant T-cell receptor (TCR) and/or Chimeric Antigen Receptor (CAR).

* * * * *

SEQUENCE LISTING

```
Sequence total quantity: 11
SEQ ID NO: 1            moltype = AA  length = 635
FEATURE                 Location/Qualifiers
REGION                  1..635
                        note = MISC_FEATURE - thrombopoietin receptor
source                  1..635
                        mol_type = protein
                        organism = Homo sapiens
SEQUENCE: 1
MPSWALFMVT SCLLLAPQNL AQVSSQDVSL LASDSEPLKC FSRTFEDLTC FWDEEEAAPS   60
GTYQLLYAYP REKPRACPLS SQSMPHFGTR YVCQFPDQEE VRLFFPLHLW VKNVFLNQTR  120
TQRVLFVDSV GLPAPPSIIK AMGGSQPGEL QISWEEPAPE ISDFLRYELR YGPRDPKNST  180
GPTVIQLIAT ETCCPALQRP HSASALDQSP CAQPTMPWQD GPKQTSPSRE ASALTAEGGS  240
```

```
CLISGLQPGN SYWLQLRSEP DGISLGGSWG SWSLPVTVDL PGDAVALGLQ CFTLDLKNVT   300
CQWQQQDHAS SQGFFYHSRA RCCPRDRYPI WENCEEEEKT NPGLQTPQFS RCHFKSRNDS   360
IIHILVEVTT APGTVHSYLG SPFWIHQAVR LPTPNLHWRE ISSGHLELEW QHPSSWAAQE   420
TCYQLRYTGE GHQDWKVLEP PLGARGGTLE LRPRSRYRLQ LRARLNGPTY QGPWSSWSDP   480
TRVETATETA WISLVTALHL VLGLSAVLGL LLLRWQFPAH YRRLRHALWP SLPDLHRVLG   540
QYLRDTAALS PPKATVSDTC EEVEPSLLEI LPKSSERTPL PLCSSQAMD  YRRLQPSCLG   600
TMPLSVCPPM AESGSCCTTH IANHSYLPLS YWQQP                              635

SEQ ID NO: 2              moltype = AA  length = 491
FEATURE                   Location/Qualifiers
REGION                    1..491
                          note = MISC_FEATURE - Extracellular domain (EC)
source                    1..491
                          mol_type = protein
                          organism = Homo sapiens
SEQUENCE: 2
MPSWALFMVT SCLLLAPQNL AQVSSQDVSL LASDSEPLKC FSRTFEDLTC FWDEEEAAPS    60
GTYQLLYAYP REKPRACPLS SQSMPHFGTR YVCQFPDQEE VRLFFPLHLW VKNVFLNQTR   120
TQRVLFVDSV GLPAPPSIIK AMGGSQPGEL QISWEEPAPE ISDFLRYELR YGPRDPKNST   180
GPTVIQLIAT ETCCPALQRP HSASALDQSP CAQPTMPWQD GPKQTSPSRE ASALTAEGGS   240
CLISGLQPGN SYWLQLRSEP DGISLGGSWG SWSLPVTVDL PGDAVALGLQ CFTLDLKNVT   300
CQWQQQDHAS SQGFFYHSRA RCCPRDRYPI WENCEEEEKT NPGLQTPQFS RCHFKSRNDS   360
IIHILVEVTT APGTVHSYLG SPFWIHQAVR LPTPNLHWRE ISSGHLELEW QHPSSWAAQE   420
TCYQLRYTGE GHQDWKVLEP PLGARGGTLE LRPRSRYRLQ LRARLNGPTY QGPWSSWSDP   480
TRVETATETA W                                                        491

SEQ ID NO: 3              moltype = AA  length = 22
FEATURE                   Location/Qualifiers
REGION                    1..22
                          note = MISC_FEATURE - Transmembrane domain (TM)
source                    1..22
                          mol_type = protein
                          organism = Homo sapiens
SEQUENCE: 3
ISLVTALHLV LGLSAVLGLL LL                                             22

SEQ ID NO: 4              moltype = AA  length = 122
FEATURE                   Location/Qualifiers
REGION                    1..122
                          note = MISC_FEATURE - Intracellular Domain (IC)
source                    1..122
                          mol_type = protein
                          organism = Homo sapiens
SEQUENCE: 4
RWQFPAHYRR LRHALWPSLP DLHRVLGQYL RDTAALSPPK ATVSDTCEEV EPSLLEILPK    60
SSERTPLPLC SSQAQMDYRR LQPSCLGTMP LSVCPPMAES GSCCTTHIAN HSYLPLSYWQ   120
QP                                                                  122

SEQ ID NO: 5              moltype = AA  length = 635
FEATURE                   Location/Qualifiers
REGION                    1..635
                          note = MISC_FEATURE - TpoR F104S
VARIANT                   104
                          note = F104S amino acid substitution
source                    1..635
                          mol_type = protein
                          organism = Homo sapiens
SEQUENCE: 5
MPSWALFMVT SCLLLAPQNL AQVSSQDVSL LASDSEPLKC FSRTFEDLTC FWDEEEAAPS    60
GTYQLLYAYP REKPRACPLS SQSMPHFGTR YVCQFPDQEE VRLSFPLHLW VKNVFLNQTR   120
TQRVLFVDSV GLPAPPSIIK AMGGSQPGEL QISWEEPAPE ISDFLRYELR YGPRDPKNST   180
GPTVIQLIAT ETCCPALQRP HSASALDQSP CAQPTMPWQD GPKQTSPSRE ASALTAEGGS   240
CLISGLQPGN SYWLQLRSEP DGISLGGSWG SWSLPVTVDL PGDAVALGLQ CFTLDLKNVT   300
CQWQQQDHAS SQGFFYHSRA RCCPRDRYPI WENCEEEEKT NPGLQTPQFS RCHFKSRNDS   360
IIHILVEVTT APGTVHSYLG SPFWIHQAVR LPTPNLHWRE ISSGHLELEW QHPSSWAAQE   420
TCYQLRYTGE GHQDWKVLEP PLGARGGTLE LRPRSRYRLQ LRARLNGPTY QGPWSSWSDP   480
TRVETATETA WISLVTALHL VLGLSAVLGL LLLRWQFPAH YRRLRHALWP SLPDLHRVLG   540
QYLRDTAALS PPKATVSDTC EEVEPSLLEI LPKSSERTPL PLCSSQAQMD YRRLQPSCLG   600
TMPLSVCPPM AESGSCCTTH IANHSYLPLS YWQQP                              635

SEQ ID NO: 6              moltype = AA  length = 319
FEATURE                   Location/Qualifiers
REGION                    1..319
                          note = MISC_FEATURE - CD34-TpoR
REGION                    133..319
                          note = MISC_FEATURE - TpoR portion
source                    1..319
                          mol_type = protein
                          organism = Homo sapiens
```

```
SEQUENCE: 6
MPRGWTALCL  LSLLPSGFMS  LDNNGTATPE  LPTQGTFSNV  STNVSYQETT  TPSTLGSTSL   60
HPVSQHGNEA  TTNITETTVK  FTSTSVITSV  YGNTNSSVQS  QTSVISTVFT  TPANVSTPET  120
TLKPSLSPGN  VSLELRPRSR  YRLQLRARLN  GPTYQGPWSS  WSDPTRVETA  TETAWISLVT  180
ALHLVLGLSA  VLGLLLLRWQ  FPAHYRRLRH  ALWPSLPDLH  RVLGQYLRDT  AALSPPKATV  240
SDTCEEVEPS  LLEILPKSSE  RTPLPLCSSQ  AQMDYRRLQP  SCLGTMPLSV  CPPMAESGSC  300
CTTHIANHSY  LPLSYWQQP                                                  319

SEQ ID NO: 7            moltype = AA  length = 698
FEATURE                 Location/Qualifiers
REGION                  1..698
                        note = MISC_FEATURE - TpoR-GCSFR
REGION                  1..513
                        note = MISC_FEATURE - TpoR portion
source                  1..698
                        mol_type = protein
                        organism = Homo sapiens
SEQUENCE: 7
MPSWALFMVT  SCLLLAPQNL  AQVSSQDVSL  LASDSEPLKC  FSRTFEDLTC  FWDEEEAAPS   60
GTYQLLYAYP  REKPRACPLS  SQSMPHFGTR  YVCQFPDQEE  VRLFFPLHLW  VKNVFLNQTR  120
TQRVLFVDSV  GLPAPPSIIK  AMGGSQPGEL  QISWEEPAPE  ISDFLRYELR  YGPRDPKNST  180
GPTVIQLIAT  ETCCPALQRP  HSASALDQSP  CAQPTMPWQD  GPKQTSPSRE  ASALTAEGGS  240
CLISGLQPGN  SYWLQLRSEP  DGISLGGSWG  SWSLPVTVDL  PGDAVALGLQ  CFTLDLKNVT  300
CQWQQQDHAS  SQGFFYHSRA  RCCPRDRYPI  WENCEEEEKT  NPGLQTPQFS  RCHFKSRNDS  360
IIHILVEVTT  APGTVHSYLG  SPFWIHAVR  LPTPNLHWRE  ISSGHLELEW  QHPSSWAAQE  420
TCYQLRYTGE  GHQDWKVLEP  PLGARGGTLE  LRPRSRYRLQ  LRARLNGPTY  QGPWSSWSDP  480
TRVETATETA  WISLVTALHL  VLGLSAVLGL  LLLPNRKNPL  WPSVPDPAHS  SLGSWVPTIM  540
EEDAFQLPGL  GTPPITKLTV  LEEDEKKPVP  WESHNSSETC  GLPTLVQTYV  LQGDPRAVST  600
QPQSQSGTSD  QVLYGQLLGS  PTSPGPGHYL  RCDSTQPLLA  GLTPSPKSYE  NLWFQASPLG  660
TLVTPAPSQE  DDCVFGPLLN  FPLLQGIRVH  GMEALGSF                           698

SEQ ID NO: 8            moltype = AA  length = 863
FEATURE                 Location/Qualifiers
REGION                  1..863
                        note = MISC_FEATURE - TpoR-HGHR
REGION                  1..513
                        note = MISC_FEATURE - TpoR portion
source                  1..863
                        mol_type = protein
                        organism = Homo sapiens
SEQUENCE: 8
MPSWALFMVT  SCLLLAPQNL  AQVSSQDVSL  LASDSEPLKC  FSRTFEDLTC  FWDEEEAAPS   60
GTYQLLYAYP  REKPRACPLS  SQSMPHFGTR  YVCQFPDQEE  VRLFFPLHLW  VKNVFLNQTR  120
TQRVLFVDSV  GLPAPPSIIK  AMGGSQPGEL  QISWEEPAPE  ISDFLRYELR  YGPRDPKNST  180
GPTVIQLIAT  ETCCPALQRP  HSASALDQSP  CAQPTMPWQD  GPKQTSPSRE  ASALTAEGGS  240
CLISGLQPGN  SYWLQLRSEP  DGISLGGSWG  SWSLPVTVDL  PGDAVALGLQ  CFTLDLKNVT  300
CQWQQQDHAS  SQGFFYHSRA  RCCPRDRYPI  WENCEEEEKT  NPGLQTPQFS  RCHFKSRNDS  360
IIHILVEVTT  APGTVHSYLG  SPFWIHAVR  LPTPNLHWRE  ISSGHLELEW  QHPSSWAAQE  420
TCYQLRYTGE  GHQDWKVLEP  PLGARGGTLE  LRPRSRYRLQ  LRARLNGPTY  QGPWSSWSDP  480
TRVETATETA  WISLVTALHL  VLGLSAVLGL  LLLKQQRIKM  LILPPVPVPK  IKGIDPDLLK  540
EGKLEEVNTI  LAIHDSYKPE  FHSDDSWVEF  IELDIDEPDE  KTEESDTDRL  LSSDHEKSHS  600
NLGVKDGDSG  RTSCCEPDIL  ETDFNANDIH  EGTSEVAQPQ  RLKGEADLLC  LDQKNQNNSP  660
YHDACPATQQ  PSVIQAEKNK  PQPLPTEGAE  STHQAAHIQL  SNPSSLSNID  FYAQVSDITP  720
AGSVVLSPGQ  KNKAGMSQCD  MHPEMVSLCQ  ENFLMDNAYF  CEADAKKCIP  VAPHIKVESH  780
IQPSLNQEDI  YITTESLTTA  AGRPGTGEHV  PGSEMPVPDY  TSIHIVQSPQ  GLILNATALP  840
LPDKEFLSSC  GYVSTDQLNK  IMP                                            863

SEQ ID NO: 9            moltype = AA  length = 877
FEATURE                 Location/Qualifiers
REGION                  1..877
                        note = MISC_FEATURE - TpoR-PrlR
REGION                  1..513
                        note = MISC_FEATURE - TpoR portion
source                  1..877
                        mol_type = protein
                        organism = Homo sapiens
SEQUENCE: 9
MPSWALFMVT  SCLLLAPQNL  AQVSSQDVSL  LASDSEPLKC  FSRTFEDLTC  FWDEEEAAPS   60
GTYQLLYAYP  REKPRACPLS  SQSMPHFGTR  YVCQFPDQEE  VRLFFPLHLW  VKNVFLNQTR  120
TQRVLFVDSV  GLPAPPSIIK  AMGGSQPGEL  QISWEEPAPE  ISDFLRYELR  YGPRDPKNST  180
GPTVIQLIAT  ETCCPALQRP  HSASALDQSP  CAQPTMPWQD  GPKQTSPSRE  ASALTAEGGS  240
CLISGLQPGN  SYWLQLRSEP  DGISLGGSWG  SWSLPVTVDL  PGDAVALGLQ  CFTLDLKNVT  300
CQWQQQDHAS  SQGFFYHSRA  RCCPRDRYPI  WENCEEEEKT  NPGLQTPQFS  RCHFKSRNDS  360
IIHILVEVTT  APGTVHSYLG  SPFWIHAVR  LPTPNLHWRE  ISSGHLELEW  QHPSSWAAQE  420
TCYQLRYTGE  GHQDWKVLEP  PLGARGGTLE  LRPRSRYRLQ  LRARLNGPTY  QGPWSSWSDP  480
TRVETATETA  WISLVTALHL  VLGLSAVLGL  LLLKGYSMVT  CIFPPVPGPK  IKGFDAHLLE  540
KGKSEELLSA  LGCQDFPPTS  DYEDLLVEYL  EVDDSEDQHL  MSVHSKEHPS  QGMKPTYLDP  600
DTDSGRGSCD  SPSLLSEKCE  EPQANPSTFY  DPEVIEKPEN  PETTHTWDPQ  CISMEGKIPY  660
FHAGGSKCST  WPLPQPSQHN  PRSSYHNITD  VCELAVGPAG  APATLLNEAG  KDALKSSQTI  720
```

```
KSREEGKATQ QREVESFHSE TDQDTPWLLP QEKTPFGSAK PLDYVEIHKV NKDGALSLLP  780
KQRENSGKPK KPGTPENNKE YAKVSGVMDN NILVLVPDPH AKNVACFEES AKEAPPSLEQ  840
NQAEKALANF TATSSKCRLQ LGGLDYLDPA CFTHSFH                           877

SEQ ID NO: 10            moltype = AA  length = 799
FEATURE                  Location/Qualifiers
REGION                   1..799
                         note = MISC_FEATURE - TpoR-IL2R?
REGION                   1..513
                         note = MISC_FEATURE - TpoR portion
source                   1..799
                         mol_type = protein
                         organism = Homo sapiens
SEQUENCE: 10
MPSWALFMVT SCLLLAPQNL AQVSSQDVSL LASDSEPLKC FSRTFEDLTC FWDEEEAAPS  60
GTYQLLYAYP REKPRACPLS SQSMPHFGTR YVCQFPDQEE VRLFFPLHLW VKNVFLNQTR  120
TQRVLFVDSV GLPAPPSIIK AMGGSQPGEL QISWEEPAPE ISDFLRYELR YGPRDPKNST  180
GPTVIQLIAT ETCCPALQRP HSASALDQSP CAQPTMPWQD GPKQTSPSRE ASALTAEGGS  240
CLISGLQPGN SYWLQLRSEP DGISLGGSWG SWSLPVTVDL PGDAVALGLQ CFTLDLKNVT  300
CQWQQQDHAS SQGFFYHSRA RCCPRDRYPI WENCEEEEKT NPGLQTPQFS RCHFKSRNDS  360
IIHILVEVTT APGTVHSYLG SPFWIHQAVR LPTPNLHWRE ISSGHLELEW QHPSSWAAQE  420
TCYQLRYTGE GHQDWKVLEP PLGARGGTLE LRPRSRYRLQ LRARLNGPTY QGPWSSWSDP  480
TRVETATETA WISLVTALHL VLGLSAVLGL LLLNCRNTGP WLKKVLKCNT PDPSKFFSQL  540
SSEHGGDVQK WLSSPFPSSS FSPGGLAPEI SPLEVLERDK VTQLLLQQDK VPEPASLSSN  600
HSLTSCFTNQ GYFFFHLPDA LEIEACQVYF TYDPYSEEDP DEGVAGAPTG SSPQPLQPLS  660
GEDDAYCTFP SRDDLLLFSP SLLGGPSPPS TAPGGSGAGE ERMPPSLQER VPRDWDPQPL  720
GPPTPGVPDL VDFQPPPELV LREAGEEVPD AGPREGVSFP WSRPPGQGEF RALNARLPLN  780
TDAYLSLQEL QGQDPTHLV                                              799

SEQ ID NO: 11            moltype = DNA  length = 1905
FEATURE                  Location/Qualifiers
misc_feature             1..1905
                         note = Codon optimised human sequence
misc_feature             1..1905
                         note = MISC_FEATURE - Codon optimised sequence based on
                          human TpoR sequence
source                   1..1905
                         mol_type = other DNA
                         organism = synthetic construct
SEQUENCE: 11
atgccctcct gggccctctt catggtcacc tcctgcctcc tcctggcccc tcaaaacctg  60
gcccaagtca gcagccaaga tgtctccttg ctggcatcag actcagagcc cctgaagtgt  120
ttctcccgaa catttgagga cctcacttgc ttctgggatg aggaagaggc agcgcccagt  180
gggacatacc agctgctgta tgcctacccg cgggagaagc ccgtgcttg cccccctgagt  240
tcccagagca tgcccacttt ggaacccga tacgtgtgcc agtttccaga ccaggaggaa  300
gtgcgtctct tctttccgct gcacctctgg gtgaagaatg tgttcctaaa ccagactcgg  360
actcagcgag tcctctttgt ggacagtgta ggcctgccgg ctccccccag tatcatcaag  420
gccatgggtg ggagccagcc aggggaactt cagatcagct gggaggagcc agctccagaa  480
atcagtgatt tcctgaggta cgaactccgc tatggcccca gagatcccaa gaactccact  540
ggtcccacgg tcatacagct gattgccaca gaaacctgct gccctgctct gcagaggcct  600
cactcagcct ctgctctgga ccagtctcca tgtgctcagc ccacaatgcc ctggcaagat  660
ggaccaaagc agacctcccc aagtagagaa gcttcagctc tgacagcaga gggtggaagc  720
tgcctcatct caggactcca gcctggcaac tcctactggc tgcagctgcg cagcgaacct  780
gatgggatct ccctcggtgg ctcctgggga tcctggtccc tccctgtgac tgtggacctg  840
cctggagatg cagtggcact tggactgcaa tgctttacct tggacctgaa gaatgttacc  900
tgtcaatggc agcaacagga ccatgctagc tcccaaggct tcttctacca cagcagggca  960
cggtgctgcc ccagagacag gtaccccatc tgggagaact gcgaagagga agagaaaaca  1020
aatccaggac tacagacccc acagttctct cgctgccact tcaagtcacg aaatgacagc  1080
attattcaca tccttgtgga ggtgaccaca gccccgggta ctgttcacag ctacctgggc  1140
tcccctttct ggatccacca ggctgtgcgc ctccccaccc caaacttgca ctggagggag  1200
atctccagtg ggcatctgga attggagtgg cagcacccat cgtcctgggc agcccaagag  1260
acctgttatc aactccgata cacaggagaa ggccatcagg actggaaggt gctggagccg  1320
cctctcgggg cccgaggagg gaccctggag ctgcgccgc gatctcgcta ccgtttacag  1380
ctgcgcgcca ggctcaacgg ccccacctac caaggtccct ggagctcgtg gtcggaccca  1440
actagggtgg agaccgccac cgagaccgcc tggatcctct tggtgaccgc tctgcatcta  1500
gtgctgggcc tcagcgccgt cctggggctg ctgctgctga ggtggcagtt tcctgcacac  1560
tacaggagac tgaggcatgc cctgtggccc tcacttccag acctgcaccg ggtcctaggc  1620
cagtaccta gggacactgc agccctgagc ccgcccaagg ccacagtcct agataccgtgt  1680
gaagaagtgg aacccagcct ccttgaaatc ctccccaagt cctcagagag gactcctttg  1740
cccctgtgtt cctccaggc ccagatggac taccgaagat tgcagccttc ttgcctgggg  1800
accatgcccc tgtctgtgtg cccacccatg gctgagtcag ggtcctgctg taccacccac  1860
attgccaacc attcctacct accactaagc tattggcagc agcct                 1905
```